US011667886B2

(12) United States Patent
Papapetridis et al.

(10) Patent No.: US 11,667,886 B2
(45) Date of Patent: *Jun. 6, 2023

(54) RECOMBINANT YEAST CELL

(71) Applicant: DSM IP Assets B.V., Heerlen (NL)

(72) Inventors: Ioannis Papapetridis, Delft (NL);
Jacobus Thomas Pronk, Delft (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/621,572

(22) PCT Filed: Jun. 4, 2018

(86) PCT No.: PCT/EP2018/064564
§ 371 (c)(1),
(2) Date: Dec. 11, 2019

(87) PCT Pub. No.: WO2018/228836
PCT Pub. Date: Dec. 20, 2018

(65) Prior Publication Data
US 2020/0157489 A1 May 21, 2020

(30) Foreign Application Priority Data

Jun. 13, 2017 (EP) .................................. 17175637
Nov. 30, 2017 (EP) .................................. 17204602
Jan. 29, 2018 (EP) .................................. 18153828

(51) Int. Cl.
*C12N 1/16* (2006.01)
*C12N 15/52* (2006.01)
*C12P 7/10* (2006.01)
*C12N 1/18* (2006.01)
*C12R 1/865* (2006.01)

(52) U.S. Cl.
CPC .............. *C12N 1/16* (2013.01); *C12N 1/185* (2021.05); *C12N 15/52* (2013.01); *C12P 7/10* (2013.01); *C12P 2203/00* (2013.01); *C12R 2001/865* (2021.05); *C12Y 101/01008* (2013.01); *C12Y 202/01001* (2013.01); *C12Y 202/01002* (2013.01); *C12Y 207/01019* (2013.01); *C12Y 401/01039* (2013.01); *C12Y 501/03001* (2013.01); *C12Y 503/01006* (2013.01)

(58) Field of Classification Search
CPC . C12N 1/16; C12N 1/85; C12N 15/52; C12N 9/0006; C12N 9/88; C12N 9/1205; C12P 7/10; C12P 2203/00; C12P 7/06; C12R 2001/865; C12Y 101/01008; C12Y 202/01001; C12Y 202/01002; C12Y 207/01019; C12Y 401/01039; C12Y 501/03001; C12Y 503/01006; Y02E 50/10
See application file for complete search history.

(56) References Cited

U.S. PATENT DOCUMENTS

| 10,689,670 | B2 * | 6/2020 | Papapetridis | ............. C12N 1/16 |
| 11,186,850 | B2 * | 11/2021 | Papapetridis | ............. C12P 7/06 |
| 2011/0165660 | A1 * | 7/2011 | Picataggio | ................ C12P 7/10 435/254.21 |
| 2015/0299713 | A1 * | 10/2015 | Jiang | ........................ C12N 9/90 435/167 |
| 2015/0353942 | A1 * | 12/2015 | Van Maris | ................ C12P 7/62 435/106 |
| 2017/0044577 | A1 * | 2/2017 | Losordo | .................... C12P 7/10 |
| 2019/0106464 | A1 * | 4/2019 | Oeser | ....................... C12P 7/065 |
| 2019/0249201 | A1 | 8/2019 | Papapetridis et al. | |
| 2020/0157489 | A1 * | 5/2020 | Papapetridis | ........ C12N 9/0006 |

FOREIGN PATENT DOCUMENTS

| WO | 2014/033019 | A1 | 3/2014 |
| WO | 2014/129898 | A2 | 8/2014 |
| WO | 2015/107496 | A1 | 7/2015 |
| WO | 2017/216136 | A1 | 12/2017 |

OTHER PUBLICATIONS

Ter Linde et al., "Genome-wide transcriptional analysis of aerobic and anaerobic chemostat cultures of *Saccharomyces cerevisiae*", Journal of Bacteriology, vol. 181, No. 24, pp. 7409-7413, 1999 (Year: 1999).*
Tai et al., "Two-dimensional transcriptome analysis in chemostat cultures. Combinatorial effects of oxygen availability and macronutrient limitation in *Saccharomyces cerevisiae*", The Journal of Biological Chemistry, vol. 280, No. 1, pp. 437-447, 2005 (Year: 2005).*
PCT International Search Report for PCT/EP2018/064564, dated Jun. 28, 2018.
Ya-Han Li et al., "The coupling of glycolysis and the Rubisco-based pathway through the non-oxidative pentose phosphate pathway to achieve low carbon dioxide emission fermentation," Biosource Technology, vol. 187, pp. 189-197, Jul. 1, 2015.
Nissen et al. Yeast 16 (2000) 463-474.
Nevoigt, E. Progress in metabolic engineering of *Saccharomyces cerevisiae*. Microbiol Mol Biol Rev. 2008;7(3):379-412.

* cited by examiner

*Primary Examiner* — Ganapathirama Raghu
(74) *Attorney, Agent, or Firm* — McBee, Moore & Vanik IP, LLC

(57) ABSTRACT

The present invention describes a recombinant yeast cell functionally expressing one or more heterologous nucleic acid sequences encoding for ribulose-1,5-phosphate carboxylase/oxygenase (EC4.1.1.39; Rubisco), and optionally one or more molecular chaperones for Rubisco, and one or more phosphoribulokinase (EC2.7.1.19; PRK), wherein one or more genes of the non-oxidative branch of the pentose phosphate pathway are overexpressed and/or wherein said yeast cell comprises a deletion or disruption of a glycerol-3-phosphate dehydrogenase (GPD) gene.

16 Claims, 1 Drawing Sheet
Specification includes a Sequence Listing.

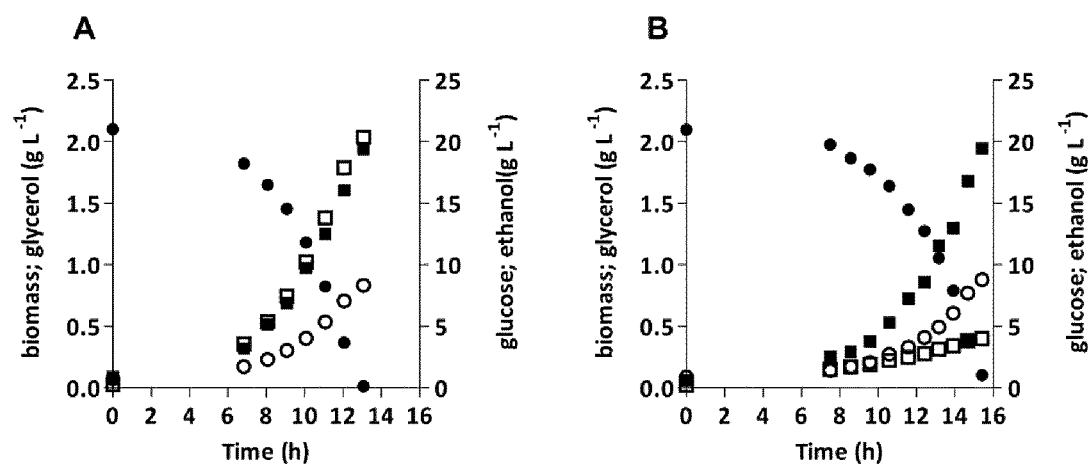

SEQUENCE LISTING

```
<160> NUMBER OF SEQ ID NOS: 9

<210> SEQ ID NO 1
<211> LENGTH: 459
<212> TYPE: PRT
<213> ORGANISM: T. dinitrificans
<220> FEATURE:
<221> NAME/KEY: MISC_FEATURE
<222> LOCATION: (1)..(459)
<223> OTHER INFORMATION: Amino acid sequence of T. denitrificans Rubisco
      large subunit CbbM
```

<400> SEQUENCE: 1

```
Met Asp Gln Ser Ala Arg Tyr Ala Asp Leu Ser Leu Lys Glu Glu Asp
1               5                   10                  15

Leu Ile Lys Gly Gly Arg His Ile Leu Val Ala Tyr Lys Met Lys Pro
            20                  25                  30

Lys Ser Gly Tyr Gly Tyr Leu Glu Ala Ala His Phe Ala Ala Glu
        35                  40                  45

Ser Ser Thr Gly Thr Asn Val Glu Val Ser Thr Asp Asp Phe Thr
    50                  55                  60

Lys Gly Val Asp Ala Leu Val Tyr Tyr Ile Asp Glu Ala Ser Glu Asp
65                  70                  75                  80

Met Arg Ile Ala Tyr Pro Leu Glu Leu Phe Asp Arg Asn Val Thr Asp
                85                  90                  95

Gly Arg Phe Met Leu Val Ser Phe Leu Thr Leu Ala Ile Gly Asn Asn
                100                 105                 110

Gln Gly Met Gly Asp Ile Glu His Ala Lys Met Ile Asp Phe Tyr Val
                115                 120                 125

Pro Glu Arg Cys Ile Gln Met Phe Asp Gly Pro Ala Thr Asp Ile Ser
                130                 135                 140

Asn Leu Trp Arg Ile Leu Gly Arg Pro Val Val Asn Gly Gly Tyr Ile
145                 150                 155                 160

Ala Gly Thr Ile Ile Lys Pro Lys Leu Gly Leu Arg Pro Glu Pro Phe
                165                 170                 175

Ala Lys Ala Ala Tyr Gln Phe Trp Leu Gly Gly Asp Phe Ile Lys Asn
                180                 185                 190

Asp Glu Pro Gln Gly Asn Gln Val Phe Cys Pro Leu Lys Lys Val Leu
                195                 200                 205

Pro Leu Val Tyr Asp Ala Met Lys Arg Ala Gln Asp Asp Thr Gly Gln
                210                 215                 220

Ala Lys Leu Phe Ser Met Asn Ile Thr Ala Asp Asp His Tyr Glu Met
225                 230                 235                 240

Cys Ala Arg Ala Asp Tyr Ala Leu Glu Val Phe Gly Pro Asp Ala Asp
                245                 250                 255

Lys Leu Ala Phe Leu Val Asp Gly Tyr Val Gly Gly Pro Gly Met Val
                260                 265                 270

Thr Thr Ala Arg Arg Gln Tyr Pro Gly Gln Tyr Leu His Tyr His Arg
                275                 280                 285

Ala Gly His Gly Ala Val Thr Ser Pro Ser Ala Lys Arg Gly Tyr Thr
                290                 295                 300

Ala Phe Val Leu Ala Lys Met Ser Arg Leu Gln Gly Ala Ser Gly Ile
305                 310                 315                 320

His Val Gly Thr Met Gly Tyr Gly Lys Met Glu Gly Glu Gly Asp Asp
                325                 330                 335

Lys Ile Ile Ala Tyr Met Ile Glu Arg Asp Glu Cys Gln Gly Pro Val
                340                 345                 350

Tyr Phe Gln Lys Trp Tyr Gly Met Lys Pro Thr Thr Pro Ile Ile Ser
                355                 360                 365

Gly Gly Met Asn Ala Leu Arg Leu Pro Gly Phe Phe Glu Asn Leu Gly
                370                 375                 380

His Gly Asn Val Ile Asn Thr Ala Gly Gly Gly Ser Tyr Gly His Ile
385                 390                 395                 400

Asp Ser Pro Ala Ala Gly Ala Ile Ser Leu Arg Gln Ser Tyr Glu Cys
                405                 410                 415
```

```
Trp Lys Gln Gly Ala Asp Pro Ile Glu Phe Ala Lys Glu His Lys Glu
                    420                 425                 430

Phe Ala Arg Ala Phe Glu Ser Phe Pro Lys Asp Ala Asp Lys Leu Phe
            435                 440                 445

Pro Gly Trp Arg Glu Lys Leu Gly Val His Ser
        450                 455

<210> SEQ ID NO 2
<211> LENGTH: 352
<212> TYPE: PRT
<213> ORGANISM: S. oleracea
<220> FEATURE:
<221> NAME/KEY: MISC_FEATURE
<222> LOCATION: (1)..(352)
<223> OTHER INFORMATION: Amino acid sequence of S. oleracea
      phosphoribulokinase (prk)

<400> SEQUENCE: 2

Met Ser Gln Gln Gln Thr Ile Val Ile Gly Leu Ala Ala Asp Ser Gly
1               5                   10                  15

Cys Gly Lys Ser Thr Phe Met Arg Arg Leu Thr Ser Val Phe Gly Gly
                20                  25                  30

Ala Ala Glu Pro Pro Lys Gly Gly Asn Pro Asp Ser Asn Thr Leu Ile
            35                  40                  45

Ser Asp Thr Thr Thr Val Ile Cys Leu Asp Asp Phe His Ser Leu Asp
    50                  55                  60

Arg Asn Gly Arg Lys Val Glu Lys Val Thr Ala Leu Asp Pro Lys Ala
65              70                  75                  80

Asn Asp Phe Asp Leu Met Tyr Glu Gln Val Lys Ala Leu Lys Glu Gly
                85                  90                  95

Lys Ala Val Asp Lys Pro Ile Tyr Asn His Val Ser Gly Leu Leu Asp
            100                 105                 110

Pro Pro Glu Leu Ile Gln Pro Lys Ile Leu Val Ile Glu Gly Leu
        115                 120                 125

His Pro Met Tyr Asp Ala Arg Val Arg Glu Leu Leu Asp Phe Ser Ile
    130                 135                 140

Tyr Leu Asp Ile Ser Asn Glu Val Lys Phe Ala Trp Lys Ile Gln Arg
145                 150                 155                 160

Asp Met Lys Glu Arg Gly His Ser Leu Glu Ser Ile Lys Ala Ser Ile
                165                 170                 175

Glu Ser Arg Lys Pro Asp Phe Asp Ala Tyr Ile Asp Pro Gln Lys Gln
            180                 185                 190

His Ala Asp Val Val Ile Glu Val Leu Pro Thr Glu Leu Ile Pro Asp
        195                 200                 205

Asp Asp Glu Gly Lys Val Leu Arg Val Arg Met Ile Gln Lys Glu Gly
    210                 215                 220

Val Lys Phe Phe Asn Pro Val Tyr Leu Phe Asp Glu Gly Ser Thr Ile
225                 230                 235                 240

Ser Trp Ile Pro Cys Gly Arg Lys Leu Thr Cys Ser Tyr Pro Gly Ile
                245                 250                 255

Lys Phe Ser Tyr Gly Pro Asp Thr Phe Tyr Gly Asn Glu Val Thr Val
            260                 265                 270

Val Glu Met Asp Gly Met Phe Asp Arg Leu Asp Glu Leu Ile Tyr Val
        275                 280                 285

Glu Ser His Leu Ser Asn Leu Ser Thr Lys Phe Tyr Gly Glu Val Thr
    290                 295                 300
```

```
Gln Gln Met Leu Lys His Gln Asn Phe Pro Gly Ser Asn Asn Gly Thr
        305                 310                 315                 320

Gly Phe Phe Gln Thr Ile Ile Gly Leu Lys Ile Arg Asp Leu Phe Glu
                325                 330                 335

Gln Leu Val Ala Ser Arg Ser Thr Ala Thr Ala Thr Ala Ala Lys Ala
                340                 345                 350

<210> SEQ ID NO 3
<211> LENGTH: 97
<212> TYPE: PRT
<213> ORGANISM: E. coli
<220> FEATURE:
<221> NAME/KEY: MISC_FEATURE
<222> LOCATION: (1)..(97)
<223> OTHER INFORMATION: Amino acid sequence of E. coli groES

<400> SEQUENCE: 3

Met Asn Ile Arg Pro Leu His Asp Arg Val Ile Val Lys Arg Lys Glu
  1               5                  10                  15

Val Glu Thr Lys Ser Ala Gly Gly Ile Val Leu Thr Gly Ser Ala Ala
                 20                  25                  30

Ala Lys Ser Thr Arg Gly Glu Val Leu Ala Val Gly Asn Gly Arg Ile
             35                  40                  45

Leu Glu Asn Gly Glu Val Lys Pro Leu Asp Val Lys Val Gly Asp Ile
         50                  55                  60

Val Ile Phe Asn Asp Gly Tyr Gly Val Lys Ser Glu Lys Ile Asp Asn
 65                  70                  75                  80

Glu Glu Val Leu Ile Met Ser Glu Ser Asp Ile Leu Ala Ile Val Glu
                 85                  90                  95

Ala

<210> SEQ ID NO 4
<211> LENGTH: 548
<212> TYPE: PRT
<213> ORGANISM: E. coli
<220> FEATURE:
<221> NAME/KEY: MISC_FEATURE
<222> LOCATION: (1)..(548)
<223> OTHER INFORMATION: Amino acid sequence of E. coli groEL

<400> SEQUENCE: 4

Met Ala Ala Lys Asp Val Lys Phe Gly Asn Asp Ala Arg Val Lys Met
  1               5                  10                  15

Leu Arg Gly Val Asn Val Leu Ala Asp Ala Val Lys Val Thr Leu Gly
                 20                  25                  30

Pro Lys Gly Arg Asn Val Val Leu Asp Lys Ser Phe Gly Ala Pro Thr
             35                  40                  45

Ile Thr Lys Asp Gly Val Ser Val Ala Arg Glu Ile Glu Leu Glu Asp
         50                  55                  60

Lys Phe Glu Asn Met Gly Ala Gln Met Val Lys Glu Val Ala Ser Lys
 65                  70                  75                  80

Ala Asn Asp Ala Ala Gly Asp Gly Thr Thr Thr Ala Thr Val Leu Ala
                 85                  90                  95

Gln Ala Ile Ile Thr Glu Gly Leu Lys Ala Val Ala Ala Gly Met Asn
                100                 105                 110

Pro Met Asp Leu Lys Arg Gly Ile Asp Lys Ala Val Thr Ala Ala Val
            115                 120                 125

Glu Glu Leu Lys Ala Leu Ser Val Pro Cys Ser Asp Ser Lys Ala Ile
        130                 135                 140
```

-continued

```
Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
            165                 170                 175

Val Glu Asp Gly Thr Gly Leu Gln Asp Glu Leu Asp Val Val Glu Gly
        180                 185                 190

Met Gln Phe Asp Arg Gly Tyr Leu Ser Pro Tyr Phe Ile Asn Lys Pro
    195                 200                 205

Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
    450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
    515                 520                 525

Ala Ala Asp Leu Gly Ala Ala Gly Gly Met Gly Gly Met Gly Gly Met
    530                 535                 540

Gly Gly Met Met
545
```

```
<210> SEQ ID NO 5
<211> LENGTH: 12
<212> TYPE: DNA
<213> ORGANISM: Artificial Sequence
<220> FEATURE:
<223> OTHER INFORMATION: PRK promoter motif
<220> FEATURE:
<221> NAME/KEY: misc_feature
<222> LOCATION: (1)..(3)
<223> OTHER INFORMATION: n = a, t, c, or g
<220> FEATURE:
<221> NAME/KEY: misc_feature
<222> LOCATION: (10)..(13)
<223> OTHER INFORMATION: n = a, t, c, or g

<400> SEQUENCE: 5
nnnattgttn nn                                                       12

<210> SEQ ID NO 6
<211> LENGTH: 8
<212> TYPE: DNA
<213> ORGANISM: Artificial Sequence
<220> FEATURE:
<223> OTHER INFORMATION: PRK promoter motif

<400> SEQUENCE: 6 tcgttyag                                                             8

<210> SEQ ID NO 7
<211> LENGTH: 12
<212> TYPE: DNA
<213> ORGANISM: Artificial Sequence
<220> FEATURE:
<223> OTHER INFORMATION: PRK promoter motif

<400> SEQUENCE: 7
aaaaattgtt ga                                                       12

<210> SEQ ID NO 8
<211> LENGTH: 8
<212> TYPE: DNA
<213> ORGANISM: Artificial Sequence
<220> FEATURE:
<223> OTHER INFORMATION: PRK promoter motif

<400> SEQUENCE: 8 tcgttyag                                                             8

<210> SEQ ID NO 9
<211> LENGTH: 11
<212> TYPE: DNA
<213> ORGANISM: Artificial Sequence
<220> FEATURE:
<223> OTHER INFORMATION: PRK promoter motif

<400> SEQUENCE: 9
aaaaattgtt g                                                        11
```

RECOMBINANT YEAST CELL

CROSS-REFERENCE TO RELATED APPLICATIONS

This application is the National Stage entry of International Application No. PCT/EP2018/064564, filed Jun. 4, 2018, which claims priority to European Patent Application No. 17175637.2, filed Jun. 13, 2017, European Patent Application No. 17204602.1, filed Nov. 30, 2017, and European Patent Application No. 18153828.1, filed Jan. 29, 2018.

REFERENCE TO SEQUENCE LISTING SUBMITTED AS A COMPLIANT ASCII TEXT FILE (.txt)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-516000_ST25.txt" created on Nov. 26, 2019, and 13,477 bytes in size) is submitted concurrently with the instant application, and the entire contents of the Sequence Listing are incorporated herein by reference.

BACKGROUND

Field

Field of the Invention

The invention relates to a recombinant yeast cell having the ability to produce a desired fermentation product, to the functional expression of heterologous peptides in a yeast cell, and to a method for producing a fermentation product wherein said yeast cell is used.

Description of Related Art

Microbial fermentation processes are applied to industrial production of a broad and rapidly expanding range of chemical compounds from renewable carbohydrate feedstocks. Especially in anaerobic fermentation processes, redox balancing of the cofactor couple NADH/NAD+ can cause important constraints on product yields. This challenge is exemplified by the formation of glycerol as major by-product in the industrial production of—for instance— fuel ethanol by *Saccharomyces cerevisiae*, a direct consequence of the need to reoxidize NADH formed in biosynthetic reactions. Ethanol production by *Saccharomyces cerevisiae* is currently, by volume, the single largest fermentation process in industrial biotechnology, but various other compounds, including other alcohols, carboxylic acids, isoprenoids, amino acids etc, are also currently produced in industrial biotechnological processes. Various approaches have been proposed to improve the fermentative properties of organisms used in industrial biotechnology by genetic modification. A major challenge relating to the stoichiometry of yeast-based production of ethanol, but also of other compounds, is that substantial amounts of NADH-dependent side-products (in particular glycerol) are generally formed as a by-product, especially under anaerobic and oxygen-limited conditions or under conditions where respiration is otherwise constrained or absent. It has been estimated that, in typical industrial ethanol processes, up to about 4 wt. % of the sugar feedstock is converted into glycerol (Nissen et al. Yeast 16 (2000) 463-474). Under conditions that are ideal for anaerobic growth, the conversion into glycerol may even be higher, up to about 10%. Glycerol production under anaerobic conditions is primarily linked to redox metabolism. During anaerobic growth of *S. cerevisiae*, sugar dissimilation occurs via alcoholic fermentation. In this process, the NADH formed in the glycolytic glyceraldehyde-3-phosphate dehydrogenase reaction is reoxidized by converting acetaldehyde, formed by decarboxylation of pyruvate to ethanol via NAD+-dependent alcohol dehydrogenase. The fixed stoichiometry of this redox-neutral dissimilatory pathway causes problems when a net reduction of NAD+ to NADH occurs elsewhere in metabolism. Under anaerobic conditions, NADH reoxidation in *S. cerevisiae* is strictly dependent on reduction of sugar to glycerol. Glycerol formation is initiated by reduction of the glycolytic intermediate dihydroxyacetone phosphate (DHAP) to glycerol 3-phosphate (glycerol-3P), a reaction catalyzed by NAD+-dependent glycerol 3-phosphate dehydrogenase. Subsequently, the glycerol 3-phosphate formed in this reaction is hydrolysed by glycerol-3-phosphatase to yield glycerol and inorganic phosphate. Consequently, glycerol is a major by-product during anaerobic production of ethanol by *S. cerevisiae*, which is undesired as it reduces overall conversion of sugar to ethanol. Further, the presence of glycerol in effluents of ethanol production plants may impose costs for waste-water treatment. WO2014/129898 describes a recombinant cell functionally heterologous nucleic acid sequences encoding for ribulose-1,5-phosphate carboxylase/oxygenase (EC 4.1.1.39; herein abbreviated as "Rubisco"), and optionally molecular chaperones for Rubisco, and phosphoribulokinase (EC 2.7.1.19; herein abbreviated as "PRK"). WO2015107496 describes a recombinant cell functionally heterologous nucleic acid sequences encoding for ribulose-1,5-phosphate carboxylase/oxygenase units RbcL, RbcS and RcbX, molecular chaperones for Rubisco GroEL and GroES. In the examples PRK is expressed with a tetracyclin-iinducible promoter TetO7, see table 5. Thereby, a process aid is needed for this promoter i.e. the additions of a compound to the propagation which adds to the cost and complexity of the process. The said compound is doxycycline, an antibiotic, which is not preferred as an additive in the ethanol fermentation process. Although the described process in WO2014/129898 is advantageous, there is a continuing need for improvement, in particular improved production of a useful organic compound, such as ethanol. Also, it would be desirable to provide a microorganism wherein NADH-dependent side-products are further reduced. Also a process is desirable wherein no additives, such as antibiotic, are needed. Further, it is desirable that the propagation characteristics of the strain are improved. These are among objects of the invention.

SUMMARY OF THE INVENTION

One or more of the aforementioned objects is realized according to the present invention that provides a recombinant yeast cell functionally expressing one or more heterologous nucleic acid sequences encoding for ribulose-1,5-phosphate carboxylase/oxygenase (EC4.1.1.39; Rubisco), and optionally one or more molecular chaperones for Rubisco, and one or more phosphoribulokinase (EC2.7.1.19; PRK), wherein one or more genes of the non-oxidative branch of the pentose phosphate pathway are overexpressed and/or wherein said yeast cell comprises a deletion or disruption of a glycerol-3-phosphate dehydrogenase (GPD) gene. Advantageously, such recombinant yeast cell has improved product yields and/or reduced side-product formation and/or improved propagation characteristics and/or absence of additives, such as antibiotic, to the fermentation process, so that the conventional fermentation process does not need to be changed.

BRIEF DESCRIPTION OF THE DRAWINGS

FIG. 1: Osmotolerance assay of engineered strains. Cells were grown on synthetic medium (180 g L-1 (1 M) glucose, initial pH 6) and incubated at 30° C. for 48 h under anaerobic conditions (10% $CO_2$). A: IME324 (GPD1 GPD2); B: IMX1443 (GPD1 gpd2Δ pDAN1-prk cbbm non-ox PPP↑, diploid); C: IMX1489 (GPD1 gpd2Δ pDAN1-prk cbbm non-ox PPP↑, haploid.

DETAILED DESCRIPTION OF THE INVENTION

The invention thus relates to a recombinant yeast cell functionally expressing one or more heterologous nucleic acid sequences encoding for ribulose-1,5-phosphate carboxylase/oxygenase (EC4.1.1.39; Rubisco), and optionally one or more molecular chaperones for Rubisco, and one or more phosphoribulokinase (EC2.7.1.19; PRK), wherein one or more genes of the non-oxidative branch of the pentose phosphate pathway are overexpressed and/or wherein said yeast cell comprises a deletion or disruption of a glycerol-3-phosphate dehydrogenase (GPD) gene.

The GPD gene may be a GPD1 and/or a GPD2 gene. Both GPD1 and GPD2 genes may be deleted or disrupted, although it is preferred that GPD2, but not GPD1 is deleted or disrupted. The GPD gene encodes for an enzyme having at least EC number 1.1.1.8.

WO2011/010923 describes methods how to delete or disrupt a glycerol-3-phosphate dehydrogenase.

In an embodiment the one or more genes of the pentose phosphate pathway that is overexpressed encodes for an enzyme selected from the list of a transaldolase (EC 2.2.1.2), a transketolase (EC 2.2.1.1), a ribose-5-phosphate isomerase (EC 5.3.1.6) and a D-ribulose-5-phosphate 3-epimerase (EC 5.1.3.1).

In another embodiment the one or more genes of the pentose phosphate pathway that is overexpressed is selected from the list of TAL1, TAL2, NQM1, TKL1, TKL2, RPE1 and RK11.

In an embodiment the PRK is under control of a promoter (herein "the PRK promoter") which has a PRK expression ratio anaerobic/aerobic of 2 or more and the Rubisco is under a constitutive promoter.

In an embodiment the PRK promoter is ROX1 repressed. ROX1 is herein Heme-dependent repressor of hypoxic gene(s); that mediates aerobic transcriptional repression of hypoxia induced genes such as COX5b and CYC7; the repressor function is regulated through decreased promoter occupancy in response to oxidative stress; and contains an HMG domain that is responsible for DNA bending activity; involved in the hyperosmotic stress resistance. ROX1 is regulated by oxygen.

In an embodiment, the PRK promoter is ROX-repressed. In an embodiment, the PRK promoter has one or more ROX1 binding motif.

In an embodiment, the PRK promoter comprises in its sequence one or more of the motif NNNATTGTTNNN. In an embodiment, the PRK promoter is the native promoter of a gene selected from the list consisting of: FET4 (FErrous Transport; YMR319C), ANB1 (ANaeroBically induced; YJR047C), YHK8 (YHR048W), DAN1 (Delayed ANaerobic; YJR150C), AAC3 (ADP/ATP Carrier; YBR085W), TIR2 (TIp1-Related; YOR010C), DIP5 (DIcarboxylic amino acid Permease; YPL265W), HEM13 (HEMe biosynthesis; YDR044W), YNR014W, YAR028W, FUN 57, COX5B (Cytochrome c OXidase; YIL111W), OYE2 (Old Yellow Enzyme; YHR179W), SUR2 (SUppressor of Rvs161 and rvs167 mutations; YDR297W), FRDS1 (Fumarate ReDuctase; YEL047C), PIS1 (Phosphatidyl Inositol Synthase; YPR113W), LAC1 (Longevity-Assurance gene Cognate (LAG1 Cognate); YKL008C), YGR035C, FRT2 (Functionally Related to TCPI; YAL028W), EUG1 (ER protein Unnecessary for Growth; YDR518W), HEM14 (HEMe biosynthesis; YER014W), ISU2 (IscU homolog; YOR226C), ERG26 (ERGosterol biosynthesis; YGL001C), MLO1 (Mitochondrially LOcalized protein; YMR252C), and SML1 (Suppressor of Mec Lethality: YML058W); in particular FET4, ANB1, YHR048W, DAN1, AAC3, TIR2, DIP5 and HEM13.

In an embodiment, the PRK promoter comprises in its sequence one or more of the motif: TCGTTYAG (SEQ ID NO:6) and/or AAAAATTGTTGA (SEQ ID NO:7).

In an embodiment, the PRK promoter is comprises in its sequence one or more sequence motif: TCGTTYAG (SEQ ID NO:8) and/or AAAAATTGTTG (SEQ ID NO:9).

In particular such PRK promoter is native promoter of a DAN (Delayed ANaerobic), TIR (TIp1-Related), or PAU (seriPAUperin family) gene. In an embodiment, the PRK promoter is the native promoter of a gene selected from the list consisting of: TIR2, DAN1, TIR4 (YOR009W), TIR3 (YIL011W), PAU7 (YAR020C), PAU5 (YFL020C), YLL064C, YGR294W, DAN3 (YBR301W; PAU24), YIL176C, YGL261C, YOL161C, PAU1 (YJL223C), PAU6 (YNR076W), DAN2 (YLR037C; PAU23), YDR542W, YIR041W, YKL224C, PAU3 (YCR104W), YLL025W, YOR394W, YHL046C, YMR325W, YAL068C, YPL282C, PAU2 (YEL049W), and PAU4 (YLR461W), in particular the PRK promoter is the native promoter of a gene selected from the list consisting of: TIR2, DAN1, TIR4, TIR3, PAU7, PAU5, YLL064C, YGR294W, DAN3, YIL176C, YGL261C, YOL161C, PAU1, PAU6, DAN2, YDR542W, YIR041W, YKL224C, PAU3, and YLL025W.

The PRK promoter may have a PRK expression ratio anaerobic/aerobic of 2 or more, preferably of 3 or more, 4 or more, 5 or more, 6 or more, 7 or more, 8 or more, 9 or more, 10 or more, 20 or more or 50 or more. This is to say that the expression of PRK may be at least a factor 2 higher under anaerobic conditions than under aerobic conditions.

"Expression" refers to the transcription of a gene into structural RNA (rRNA, tRNA) or messenger RNA (mRNA) with subsequent translation into a protein.

In an embodiment the PRK expression ratio is determined by measuring the amount of PRK protein of cells grown under aerobic and anaerobic conditions. The amount of PRK protein can be determined by proteomics, as shown in the Examples.

In another embodiment the level or PRK expression ratio is determined by measuring the PRK activity of cells grown under aerobic and anaerobic conditions, e.g. in a cell-free extract. Methods to measure PRK activity are for instance described in Example 1 of pending European Patent Application EP16174382.8.

In yet another embodiment the level or PRK expression ratio is determined by measuring the transcription level (e.g. as amount of mRNA) of the PRK gene of cells grown under aerobic and anaerobic conditions. The skilled person knows how to determine translation levels using methods commonly known in the art, e.g. Q-PCR, real-time PCR, northern blot, RNA-seq.

As used herein "promoter" is a DNA sequence that directs the transcription of a (structural) gene, in particular one or more phosphoribulokinase gene. The promoter enables higher expression during anaerobic conditions than under aerobic conditions.

In an embodiment, the PRK promoter may be a synthetic oligonucleotide. It may be a product of artificial oligonucleotide synthesis. Artificial oligonucleotide synthesis is a method in synthetic biology that is used to create artificial oligonucleotides, such as genes, in the laboratory. Commercial gene synthesis services are now available from numerous companies worldwide, some of which have built their business model around this task. Current gene synthesis approaches are most often based on a combination of organic chemistry and molecular biological techniques and entire genes may be synthesized "de novo", without the need for precursor template DNA.

In an embodiment, the promoter is located in the 5-region of a the PRK gene, In an embodiment it is located proximal to the transcriptional start site of PRK gene.

The invention further relates to a process for preparing an organic compound, in particular an alcohol, comprising converting a carbon source, in particular a carbohydrate or another organic carbon source using a yeast cell, thereby forming the organic compound, wherein the yeast cell is a yeast cell according to the invention.

The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "compound", this means "at least one" of that moiety, e.g. "at least one compound", unless specified otherwise. The term 'or' as used herein is to be understood as 'and/or'.

When referring to a compound of which several isomers exist (e.g. a D and an L enantiomer), the compound in principle includes all enantiomers, diastereomers and cis/trans isomers of that compound that may be used in the particular method of the invention; in particular when referring to such as compound, it includes the natural isomer(s).

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the yeast cell, in particular a yeast cell, and usually corresponds to an oxygen consumption of less than 5 mmol/l·h, in particular to an oxygen consumption of less than 2.5 mmol/l·h, or less than 1 mmol/l·h. More preferably 0 mmol/L/h is consumed (i.e. oxygen consumption is not detectable. This usually corresponds to a dissolved oxygen concentration in the culture broth of less than 5% of air saturation, in particular to a dissolved oxygen concentration of less than 1% of air saturation, or less than 0.2% of air saturation.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well-known species.

The term "recombinant (cell)" or "recombinant microorganism" as used herein, refers to a strain (cell) containing nucleic acid which is the result of one or more genetic modifications using recombinant DNA technique(s) and/or another mutagenic technique(s). In particular a recombinant cell may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant (cell)" in particular relates to a strain (cell) from which DNA sequences have been removed using recombinant DNA techniques.

The term "transgenic (yeast) cell" as used herein, refers to a strain (cell) containing nucleic acid not naturally occurring in that strain (cell) and which has been introduced into that strain (cell) using recombinant DNA techniques, i.e. a recombinant cell).

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively of quantitatively altered function or the knock-out of that gene.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at chem.qmul.ac.uk/iubmb/enzyme/. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found via ncbi.nlm.nih.gov/, (as available on 14 Jun. 2016) unless specified otherwise.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

The term "functional homologue" (or in short "homologue") of a polypeptide having a specific sequence (e.g. SEQ ID NO: X), as used herein, refers to a polypeptide comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant yeast cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity in the yeast cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon(pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99% and having the required enzymatic functionality. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss-.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labeled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. In an embodiment, conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. In an embodiment, conservative substitutions for each of the naturally occurring amino acids are as follows: Ala to Ser; Arg to Lys; Asn to Gln or His; Asp to Glu; Cys to Ser or Ala; Gln to Asn; Glu to Asp; Gly to Pro; His to Asn or Gln; Ile to Leu or Val; Leu to lie or Val; Lys to Arg; Gln or Glu; Met to Leu or lie; Phe to Met, Leu or Tyr; Ser to Thr; Thr to Ser; Trp to Tyr; Tyr to Trp or Phe; and, Val to lie or Leu.

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength.

Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system.

In some embodiments, transformed/transfected yeast cells may be employed as expression systems for the expression of the enzymes. Expression of heterologous proteins in yeast is well known. Sherman, F., et al., Methods in Yeast Genetics, Cold Spring Harbor Laboratory (1982) is a well-recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5-region of a gene, proximal to the transcriptional start site of a (structural) gene. Promoter sequences may be constitutive, inducible or repressible. In an embodiment there is no (external) inducer needed.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

By "host cell" is meant a cell which contains a vector and supports the replication and/or expression of the vector.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

The recombinant yeast cell is preferably selected from the group of Saccharomycetaceae, such as *Saccharomyces cerevisiae, Saccharomyces pastorianus, Saccharomyces beticus, Saccharomyces fermentati, Saccharomyces paradoxus, Saccharomyces uvarum* and *Saccharomyces bayanus; Schizosaccharomyces* such as *Schizosaccharomyces pombe, Schizosaccharomyces japonicus, Schizosaccharomyces octosporus* and *Schizosaccharomyces cryophilus; Torulaspora* such as *Torulaspora delbrueckii; Kluyveromyces* such as *Kluyveromyces marxianus; Pichia* such as *Pichia stipitis, Pichia pastoris* or *pichia angusta, Zygosaccharomyces* such as *Zygosaccharomyces bailii; Brettanomyces* such as *Brettanomyces intermedius, Brettanomyces bruxellensis, Brettanomyces anomalus, Brettanomyces custersianus, Brettanomyces naardenensis, Brettanomyces nanus, Dekkera Bruxellis* and *Dekkera anomala; Metschnikowia, Issatchenkia,* such as *Issatchenkia orientalis, Kloeckera* such as *Kloeckera apiculata; Aureobasisium* such as *Aureobasidium pullulans.*

In an embodiment, the yeast cell is selected from the group of Saccharomycetaceae. In particular, good results have been achieved with a *Saccharomyces cerevisiae* cell.

The Rubisco may in principle be selected from eukaryotic and prokaryotic Rubiscos. The Rubisco is preferably from a non-phototrophic organism. In particular, the Rubisco may be from a chemolithoautotrophic microorganism. Good results have been achieved with a bacterial Rubisco.

Preferably, the bacterial Rubisco originates from a *Thiobacillus*, in particular, *Thiobacillus denitrificans*, which is chemolithoautotrophic. The Rubisco may be a single-subunit Rubisco or a Rubisco having more than one subunit. In particular, good results have been achieved with a single-subunit Rubisco. In particular, good results have been achieved with a form-II Rubisco, more in particular CbbM. A suitable Rubisco in accordance with the invention is encoded by the cbbMgene from *Thiobacillus denitrificans*. An alternative to this Rubisco, is a functional homologue of this Rubisco, in particular such functional homologue comprising a sequence having at least 80%, 85%, 90% or 95% sequence identity with the cbbM gene from *Thiobacillus denitrificans*. Suitable natural Rubisco polypeptides are given in Table 1, with identity to the cbbMgene from *Thiobacillus denitrificans*.

TABLE 1

Natural Rubisco polypeptides suitable for expression

| Source | Accession no. | MAX ID (%) |
| --- | --- | --- |
| *Thiobacillus denitrificans* | AAA99178.2 | 100 |
| *Sideroxydans lithotrophicus* ES-1 | YP_003522651.1 | 94 |
| *Thiothrix nivea* DSM 5205 | ZP_10101642.1 | 91 |
| *Halothiobacillus neapolitanus* c2 | YP_003262978.1 | 90 |
| *Acidithiobacillus ferrooxidans* ATCC 53993 | YP_002220242.1 | 88 |
| *Rhodoferax ferrireducens* T118 | YP_522655.1 | 86 |
| *Thiorhodococcus drewsii* AZ1 | ZP_08824342.1 | 85 |
| uncultured prokaryote | AGE14067.1 | 82 |

In accordance with the invention, Rubisco is functionally expressed in the microorganism, at least during use in an industrial process for preparing a compound of interest.

To increase the likelihood that herein enzyme activity is expressed at sufficient levels and in active form in the transformed (recombinant) host cells of the invention, the nucleotide sequence encoding these enzymes, as well as the Rubisco enzyme and other enzymes of the invention (see below), are preferably adapted to optimise their codon usage to that of the host cell in question. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. In an embodiment, the sequences which have been codon optimised for expression in the fungal host cell in question such as e.g. *S. cerevisiae* cells.

Preferably the functionally expressed RuBisCO has an activity, defined by the rate of ribulose-1,5-bisphosphate-dependent $^{14}$C-bicarbonate incorporation by cell extracts of at least 1 nmol·min$^{-1}$·(mg protein)$^{-1}$, in particular an activity of at least 2 nmol·min$^{-1}$·(mg protein)$^{-1}$, more in particular an activity of at least 4 nmol·min$^{-1}$·(mg protein)$^{-1}$. The upper limit for the activity is not critical. In practice, the activity may be about 200 nmol·min$^{-1}$·(mg protein)$^{-1}$ or less, in particular 25 nmol·min$^{-1}$·(mg protein)$^{-1}$, more in particular 15 nmol·min$^{-1}$·(mg protein)$^{-1}$ or less, e.g. about 10 nmol·min$^{-1}$·(mg protein)$^{-1}$ or less. The conditions for an assay for determining this Rubisco activity are as found in the Examples.

The RuBisCO nucleic acid sequence may be from *Thiobacillus denitrificans*, or it may encode a polypeptide having an amino acid acid sequence according to SEQ ID NO: 1, or it or it is a functional homogue thereof having an amino acid sequence having at least 50%, at least 60%, at least 70% sequence identity with SEQ ID NO: 1; preferably at least 80%, at least 85%, 90%, at least 95%, at least 98%, at least 99% sequence identity with SEQ ID NO: 1, or it is a functional homologue which is derived, by way of one or more amino acid substitutions, deletions or insertions, from the amino acid sequence of SEQ ID NO: 1.

A functionally expressed phosphoribulokinase (PRK, (EC 2.7.1.19)) according to the invention is capable of catalyzing the chemical reaction:

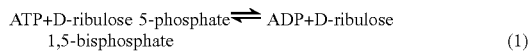
(1)

Thus, the two substrates of this enzyme are ATP and D-ribulose 5-phosphate; its two products are ADP and D-ribulose 1,5-bisphosphate.

The PRK nucleic acid sequence may be from *Spinacia oleracea*, or it may encode a polypeptide having an amino acid acid sequence according to SEQ ID NO: 2, or it or it is a functional homogue thereof having an amino acid sequence having at least 50%, at least 60%, at least 70% sequence identity with SEQ ID NO: 2; preferably at least 80%, at least 85%, 90%, at least 95%, at least 98%, at least 99% sequence identity with SEQ ID NO: 2, or it is a functional homologue which is derived, by way of one or more amino acid substitutions, deletions or insertions, from the amino acid sequence of SEQ ID NO: 2.

PRK belongs to the family of transferases, specifically those transferring phosphorus-containing groups (phosphotransferases) with an alcohol group as acceptor. The systematic name of this enzyme class is ATP:D-ribulose-5-phosphate 1-phosphotransferase. Other names in common use include phosphopentokinase, ribulose-5-phosphate kinase, phosphopentokinase, phosphoribulokinase (phosphorylating), 5-phosphoribulose kinase, ribulose phosphate kinase, PKK, PRuK, and PRK. This enzyme participates in carbon fixation. The PRK can be from a prokaryote or a eukaryote. Good results have been achieved with a PRK originating from a eukaryote. Preferably the eukaryotic PRK originates from a plant selected from Caryophyllales, in particular from Amaranthaceae, more in particular from *Spinacia*. As an alternative to PRK from *Spinacia* a functional homologue of PRK from *Spinacia* may be present, in particular a functional homologue comprising a sequence having at least 70%, 75%, 80%. 85%, 90% or 95% sequence identity with the PRK from *Spinacia*. Suitable natural PRK polypeptides are given in Table 2.

TABLE 2

Natural PRK polypeptides suitable for expression with identity to PRK from *Spinacia*

| Source | Accession no. | MAX ID (%) |
| --- | --- | --- |
| Spinacia oleracea | P09559.1 | 100 |
| Medicago truncatula | XP_003612664.1 | 88 |
| Arabidopsis thaliana | NP_174486.1 | 87 |
| Vitis vinifera | XP_002263724.1 | 86 |
| Closterium peracerosum | BAL03266.1 | 82 |
| Zea mays | NP_001148258.1 | 78 |

In an embodiment the recombinant microorganism further comprises a nucleic acid sequence encoding one or more heterologous prokaryotic or eukaryotic molecular chaperones, which—when expressed—are capable of functionally interacting with an enzyme in the microorganism, in particular with at least one of Rubisco and PRK.

Chaperonins are proteins that provide favourable conditions for the correct folding of other proteins, thus preventing aggregation. Newly made proteins usually must fold from a linear chain of amino acids into a three-dimensional form. Chaperonins belong to a large class of molecules that assist protein folding, called molecular chaperones. The energy to fold proteins is supplied by adenosine triphosphate (ATP). A review article about chaperones that is useful herein is written by Yébenes (2001); "Chaperonins: two rings for folding"; Hugo Yébenes et al. Trends in Biochemical Sciences, August 2011, Vol. 36, No. 8.

In an embodiment the chaperone or chaperones are from a bacterium, more preferably from *Escherichia*, in particular *E. coli* GroEL and GroEs from *E. coli* may in particular encoded in a microorganism according to the invention. In an embodiment, chaperones are chaperones from *Saccharomyces*, in particular *Saccharomyces cerevisiae* Hsp10 and Hsp60. If the chaperones are naturally expressed in an organelle such as a mitochondrion (examples are Hsp60 and Hsp10 of *Saccharomyces cerevisiae*) relocation to the cytosol can be achieved e.g. by modifying the native signal sequence of the chaperonins. In eukaryotes the proteins Hsp60 and Hsp10 are structurally and functionally nearly identical to GroEL and GroES, respectively. Thus, it is contemplated that Hsp60 and Hsp10 from any recombinant yeast cell may serve as a chaperone for the Rubisco. See Zeilstra-Ryalls J, Fayet O, Georgopoulos C (1991). "The universally conserved GroE (Hsp6) chaperonins". Annu Rev Microbial. 45: 301-25. doi:10.1146/annurev.mi.45.100191.001505. PMID 1683763 and Horwich A L, Fenton W A, Chapman E, Farr G W (2007). "Two Families of Chaperonin: Physiology and Mechanism". Annu Rev Cell Dev Biol. 23: 115-45. doi:10.1146/annurev.cellbio.23.090506.123555. PMID 17489689. Good results have been achieved with a recombinant yeast cell comprising both the heterologous chaperones GroEL and GroES. As an alternative to GroES a functional homologue of GroES may be present, in particular a functional homologue comprising a sequence having at least 70%, 75%, 80%, 85%, 90% or 95% sequence identity with GroES. Suitable natural chaperones polypeptide homologous to GroES are given in Table 3.

TABLE 3

Natural chaperones homologous to GroES polypeptides suitable for expression

>gi|115388105|ref|XP_001211558.1|: 2-101 10 kDa heat shock protein, mitochondrial [*Aspergillus terreus* NIH2624]
>gi|116196854|ref|XP_001224239.1|: 1-102 conserved hypothetical protein [*Chaetomium globosum* CBS 148.51]
>gi|119175741|ref|XP_001240050.1|: 3-102 hypothetical protein CIMG_09671 [*Coccidioides immitis* RS]
>gi|119471607|ref|XP_001258195.1|: 12-111 chaperonin, putative [*Neosartorya fischeri* NRRL181]
>gi|121699818|ref|XP_001268174.1|: 8-106 chaperonin, putative [*Aspergillus clavatus* NRRL 1]
>gi|126274604|ref|XP_001387607.1|: 2-102 predicted protein [*Scheffersomyces stipitis* CBS 6054]
>gi|146417701|ref|XP_001484818.1|: 5-106 conserved hypothetical protein [*Meyerozyma guilliermondii* ATCC 6260]
>gi|154303611|ref|XP_001552212.1|: 1-102 10 kDa heat shock protein, mitochondrial [*Botryotinia fuckeliana* B05.10]
>gi|156049571|ref|XP_001590752.1|: 1-102 hypothetical protein SS1G_08492 [*Sclerotinia sclerotiorum* 1980]
>gi|156840987|ref|XP_001643870.1|: 1-103 hypothetical protein Kpol_495p10 [*Vanderwaltozyma polyspora* DSM 70924]
>gi|169608295|ref|XP_001797567.1|: 1-101 hypothetical protein SNOG_07218 [*Phaeosphaeria nodorum* SN15]
>gi|171688384|ref|XP_001909132.1|: 1-102 hypothetical protein [*Podospora anserina* S mat+]
>gi|189189366|ref|XP_001931022.1|: 71-168 10 kDa chaperonin [*Pyrenophora tritici-repentis* Pt-1C-BFP]
>gi|19075598|ref|NP_588098.1|: 1-102 mitochondrial heat shock protein Hsp10 (predicted) [*Schizosaccharomyces pombe* 972h-]
>gi|212530240|ref|XP_002145277.1|: 3-100 chaperonin, putative [*Talaromyces marneffei* ATCC 18224]
>gi|212530242|ref|XP_002145278.1|: 3-95 chaperonin, putative [*Talaromyces marneffei* ATCC 18224]
>gi|213404320|ref|XP_002172932.1|: 1-102 mitochondrial heat shock protein Hsp10 [*Schizosaccharomyces japonicus* yFS275]
>gi|225557301|gb|EEH05587.1|: 381-478 pre-mRNA polyadenylation factor fip1 [*Ajellomyces capsulatus* G186AR]
>gi|225684092|gb|EEH22376.1|: 3-100 heat shock protein [*Paracoccidioides brasiliensis* Pb03]
>gi|238490530|ref|XP_002376502.1|: 2-104 chaperonin, putative [*Aspergillus flavus* NRRL3357]
>gi|238878220|gb|EEQ41858.1|: 1-106 10 kDa heat shock protein, mitochondrial [*Candida albicans* WO-1]
>gi|240280207|gb|EER43711.1|: 426-523 pre-mRNA polyadenylation factor fip1 [*Ajellomyces capsulatus* H143]
>gi|241950445|ref|XP_002417945.1|: 1-103 10 kda chaperonin, putative; 10 kda heat shock protein mitochondrial (hsp10), putative [*Candida dubliniensis* CD36]
>gi|242819222|ref|XP_002487273.1|: 90-182 chaperonin, putative [*Talaromyces stipitatus* ATC
>gi|254566327|ref|XP_002490274.1|: 1-102 Putative protein of unknown function [*Komagataella pastoris* GS115]
>gi|254577241|ref|XP_002494607.1|: 1-103 ZYRO0A05434p [*Zygosaccharomyces rouxii*]
>gi|255717999|ref|XP_002555280.1|: 1-103 KLTH0G05588p [*Lachancea thermotolerans*]
>gi|255956581|ref|XP_002569043.1|: 2-101 Pc21g20560 [*Penicillium chrysogenum* Wisconsin 54-1255]
>gi|258572664|ref|XP_002545094.1|: 16-108 chaperonin GroS [*Uncinocarpus reesii* 1704]
>gi|261190594|ref|XP_002621706.1|: 3-100 chaperonin [*Ajellomyces dermatitidis* SLH14081]
>gi|295664909|ref|XP_002793006.1|: 3-100 10 kDa heat shock protein, mitochondrial [*Paracoccidioides* sp. 'lutzii'Pb01]
>gi|296412657|ref|XP_002836039.1|: 76-177 hypothetical protein [*Tuber melanosporum* Mel28]
>gi|302307854|ref|NP_984626.2|: 2-102 AEL235Wp [*Ashbya gossypii* ATCC 10895]
>gi|302894117|ref|XP_003045939.1|: 1-102 predicted protein [*Nectria haematococca* mpVI 77-13-4]
>gi|303318351|ref|XP_003069175.1|: 3-100 10 kDa heat shock protein, mitochondrial, putative [*Coccidioides posadasii* C735 delta SOWgp]
>gi|310795300|gb|EFQ30761.1|: 1-102 chaperonin 10 kDa subunit [*Glomerella graminicola* M1.001]
>gi|315053085|ref|XP_003175916.1|: 12-109 chaperonin GroS [*Arthroderma gypseum* CBS 118893]
>gi|317032114|ref|XP_001394060.2|: 334-433 heat shock protein [*Aspergillus niger* CBS 513.88]

TABLE 3-continued

Natural chaperones homologous to GroES polypeptides suitable for expression

>gi|317032116|ref|XP_001394059.2|: 2-101 heat shock protein [*Aspergillus niger* CBS 513.88]
>gi|320583288|gb|EFW97503.1|: 6-106 chaperonin, putative heat shock protein, putative [*Ogataea parapolymorpha* DL-1]
>gi|320591507|gb|EFX03946.1|: 1-102 heat shock protein [*Grosmannia clavigera* kw1407]
>gi|322700925|gb|EFY92677.1|: 1-102 chaperonin [*Metarhizium acridum* CQMa 102]
>gi|325096696|gb|EGC50006.1|: 409-506 pre-mRNA polyadenylation factor fip1 [*Ajellomyces capsulatus* H88]
>gi|326471604|gb|EGD95613.1|: 14-111 chaperonin 10 Kd subunit [*Trichophyton tonsurans* CBS112818]
>gi|327293056|ref|XP_003231225.1|: 3-100 chaperonin [*Trichophyton rubrum* CBS 118892]
>gi|330942654|ref|XP_003306155.1|: 37-136 hypothetical protein PTT_19211 [*Pyrenophora teres f. teres* 0-1]
>gi|336268042|ref|XP_003348786.1|: 47-147 hypothetical protein SMAC_01809 [*Sordaria macrospora* khell]
>gi|340519582|gb|EGR49820.1|: 1-109 predicted protein [*Trichoderma reesei* QM6a]
>gi|340960105|gb|EGS21286.1|: 3-103 putative mitochondrial 10 kDa heat shock protein [*Chaetomium thermophilum* var. *thermophilum* DSM 1495]
>gi|342883802|gb|EGU84224.1|: 1-102 hypothetical protein FOXB_05181 [*Fusarium oxysporum* Fo5176]
>gi|344302342|gb|EGW32647.1|: 2-102 hypothetical protein SPAPADRAFT_61712 [*Spathaspora passalidarum* NRRL Y-27907]
>gi|345570750|gb|EGX53571.1|: 1-102 hypothetical protein AOL_s00006g437 [*Arthrobotrys oligospora* ATCC 24927]
>gi|346321154|gb|EGX90754.1|: 1-102 chaperonin [*Cordyceps militaris* CM01]
>gi|346970393|gb|EGY13845.1|: 1-102 heat shock protein [*Verticillium dahliae* VdLs.17]
>gi|354548296|emb|CCE45032.1|: 1-106 hypothetical protein CPAR2_700360 [*Candida parapsilosis*]
>gi|358385052|gb|EHK22649.1|: 1-102 hypothetical protein TRIVIDRAFT_230640 [*Trichoderma virens* Gv 29-8]
>gi|358393422|gb|EHK42823.1|: 1-101 hypothetical protein TRIATDRAFT_258186 [*Trichoderma atroviride* IMI 206040]
>gi|361126733|gb|EHK98722.1|: 1-97 putative 10 kDa heat shock protein, mitochondrial [*Glarea lozoyensis* 74030]
>gi|363753862|ref|XP_003647147.1|: 2-102 hypothetical protein Ecym_5593 [*Eremothecium cymbalariae* DBVPG#7215]
>gi|365758401|gb|EHN00244.1|: 1-106 Hsp10p [*Saccharomyces cerevisiae* × *Saccharomyces kudriavzevii* VIN7]
>gi|365987664|ref|XP_003670663.1|: 1-103 hypothetical protein NDAI_0F01010 [*Naumovozyma dairenensis* CBS 421]
>gi|366995125|ref|XP_003677326.1|: 1-103 hypothetical protein NCAS_0G00860 [*Naumovozyma castellii* CBS 4309]
>gi|366999797|ref|XP_003684634.1|: 1-103 hypothetical protein TPHA_0C00430 [*Tetrapisispora phaffii* CBS 4417]
>gi|367009030|ref|XP_003679016.1|: 1-103 hypothetical protein TDEL_0A04730 [*Torulaspora delbrueckii*]
>gi|367023138|ref|XP_003660854.1|: 1-104 hypothetical protein MYCTH_59302 [*Myceliophthora thermophila* ATCC 42464]
>gi|367046344|ref|XP_003653552.1|: 1-102 hypothetical protein THITE_2116070 [*Thielavia terrestris* NRRL8126]
>gi|378726440|gb|EHY52899.1|: 9-109 chaperonin GroES [*Exophiala dermatitidis* NIH/UT8656]
>gi|380493977|emb|CCF33483.1|: 1-102 chaperonin 10 kDa subunit [*Colletotrichum higginsianu*
>gi|385305728|gb|EIF49680.1|: 1-102 10 kda heat shock mitochondrial [*Dekkera bruxellensis* AWRI1499]
>gi|389628546|ref|XP_003711926.1|: 1-102 hsp10-like protein [*Magnaporthe oryzae* 70-15]
>gi|396462608|ref|XP_003835915.1|: 1-101 similar to 10 kDa heat shock protein [*Leptosphaeria maculans* JN3]
>gi|398392541|ref|XP_003849730.1|: 1-102 hypothetical protein MYCGRDRAFT_105721 [*Zymoseptoria tritici* IPO323]
>gi|400597723|gb|EJP65453.1|: 24-124 chaperonin 10 kDa subunit [*Beauveria bassiana* ARSEF 2860]
>gi|401623646|gb|EJS41738.1|: 1-106 hsp10p [*Saccharomyces arboricola* H-6]
>gi|401842164|gb|EJT44422.1|: 1-92 HSP10-like protein [*Saccharomyces kudriavzevii* IFO 1802]
>gi|402084027|gb|EJT79045.1|: 1-102 hsp10-like protein [*Gaeumannomyces graminis* var. *triti*
>gi|403215209|emb|CCK69709.1|: 1-104 hypothetical protein KNAG_0C06130 [*Kazachstania naganishii* CBS 8797]
>gi|406604629|emb|CCH43969.1|: 4-100 hypothetical protein BN7_3524 [*Wickerhamomyces ciferrii*]

TABLE 3-continued

Natural chaperones homologous to GroES polypeptides suitable for expression

>gi|406867021|gb|EKD20060.1|: 56-156 hypothetical protein MBM_02012 [*Marssonina brunnea* f. sp. 'multigermtubi' MB_m1]
>gi|407926227|gb|EKG19196.1|: 74-174 GroES-like protein [*Macrophomina phaseolina* MS6]
>gi|408398157|gb|EKJ77291.1|: 11-111 hypothetical protein FPSE_02566 [*Fusarium pseudograminearum* CS3096]
>gi|410082063|ref|XP_003958610.1|: 1-103 hypothetical protein KAFR_0H00660 [*Kazachstania africana* CBS2517]
>gi|425777664|gb|EKV15823.1|: 58-157 Chaperonin, putative [*Penicillium digitatum* Pd1]
>gi|440639680|gb|ELR09599.1|: 1-102 chaperonin GroES [*Geomyces destructans* 20631-21]
>gi|444323906|ref|XP_004182593.1|: 1-105 hypothetical protein TBLA_0J00760 [*Tetrapisisporablattae* CBS 6284]
>gi|448083208|ref|XP_004195335.1|: 2-101 Piso0_005888 [*Millerozyma farinosa* CBS 7064]
>gi|448087837|ref|XP_004196425.1|: 2-102 Piso0_005888 [*Millerozyma farinosa* CBS 7064]
>gi|448534948|ref|XP_003870866.1|: 1-106 Hsp10 protein [*Candida orthopsilosis* Co 90-125]
>gi|449295977|gb|EMC91998.1|: 1-102 hypothetical protein BAUCODRAFT_39148 [*Baudoinia compn*
>gi|46123659|ref|XP_386383.1|: 3-103 hypothetical protein FG06207.1 [*Gibberella zeae* PH-1]
>gi|50289455|ref|XP_447159.1|: 1-103 hypothetical protein [*Candida glabrata* CBS 138]
>gi|50308731|ref|XP_454370.1|: 1-103 hypothetical protein [*Kluyveromyces lactis* NRRL Y-1140]
>gi|50411066|ref|XP_457014.1|: 1-106 DEHA2B01122p [*Debaryomyces hansenii* CBS767]
>gi|50545998|ref|XP_500536.1|: 1-102 YALI0B05610p [*Yarrowia lipolytica*]
>gi|51013895|gb|AAT93241.1|: 1-106 YOR020C [*Saccharomyces cerevisiae*]
>gi|6324594|ref|NP_014663.1|: 1-106 Hsp10p [*Saccharomyces cerevisiae* S288c]
>gi|67523953|ref|XP_660036.1|: 2-101 hypothetical protein AN2432.2 [*Aspergillus nidulans* FGSC A4]
>gi|70992219|ref|XP_750958.1|: 12-106 chaperonin [*Aspergillus fumigatus* Af293]
>gi|85079266|ref|XP_956315.1|: 1-104 hypothetical protein NCU04334 [*Neurospora crassa* OR74A]

As an alternative to GroEL a functional homologue of GroEL may be present, in particular a functional homologue comprising a sequence having at least 70%, 75%, 80%, 85%, 90% or 95% sequence identity with SEQUENCE of GroEL. Suitable natural chaperones polypeptides homologous to GroEL are given in Table 4.

TABLE 4

Natural chaperones homologous to GroEL polypeptides suitable for expression

>gi|115443330|ref|XP_001218472.1| heat shock protein 60, mitochondrial precursor [*Aspergillus terreus* NIH2624]
>gi|114188341|gb|EAU30041.1| heat shock protein 60, mitochondrial precursor [*Aspergillus terreus* NIH2624]
>gi|119480793|ref|XP_001260425.1| antigenic mitochondrial protein HSP60, putative [*Neosartorya fischeri* NRRL 181] >gi|119408579|gb|EAW18528.1| antigenic mitochondrial protein HSP60, putative [*Neosartorya fischeri* NRRL 181]
>gi|126138730|ref|XP_001385888.1| hypothetical protein PICST_90190 [*Scheffersomyces stipitis* CBS 6054] >gi|126093166|gb|ABN67859.1| mitochondrial groEL-type heat shock protein [*Scheffersomyces stipitis* CBS 6054]
>gi|145246630|ref|XP_001395564.1| heat shock protein 60 [*Aspergillus niger* CBS 513.88] >gi|134080285|emb|CAK46207.1| unnamed protein product [*Aspergillus niger*] >gi|350636909|gb|EHA25267.1| hypothetical protein ASPNIDRAFT_54001 [*Aspergillus niger* ATCC 1015]
>gi|146413148|ref|XP_001482545.1| heat shock protein 60, mitochondrial precursor [*Meyerozyma guilliermondii* ATCC 6260]
>gi|154277022|ref|XP_001539356.1| heat shock protein 60, mitochondrial precursor [*Ajellomyces capsulatus* NAm1] >gi|150414429|gb|EDN09794.1| heat shock protein 60, mitochondrial precursor [*Ajellomyces capsulatus* NAm1]
>gi|154303540|ref|XP_001552177.1| heat shock protein 60 [*Botryotinia fuckeliana* B05.10] >gi|347840915|emb|CCD55487.1| similar to heat shock protein 60 [*Botryotinia fuckeliana*]
>gi|156063938|ref|XP_001597891.1| heat shock protein 60, mitochondrial precursor [*Sclerotinia sclerotiorum* 1980] >gi|154697421|gb|EDN97159.1| heat shock protein 60, mitochondrial precursor [*Sclerotinia sclerotiorum* 1980 UF-70]

TABLE 4-continued

Natural chaperones homologous to GroEL polypeptides suitable for expression

>gi|156844469|ref|XP_001645297.1| hypothetical protein Kpol_1037p35
[*Vanderwaltozyma polyspora* DSM 70294] >gi|156115957|gb|EDO17439.1|
hypothetical protein Kpol_1037p35 [*Vanderwaltozyma polyspora* DSM 70294]
>gi|16416029|emb|CAB91379.2| probable heat-shock protein hsp60 [*Neurospora crassa*] >gi|350289516|gb|EGZ70741.1| putative heat-shock protein hsp60
[*Neurospora tetrasperma* FGSC 2509]
>gi|169626377|ref|XP_001806589.1| hypothetical protein SNOG_16475
[*Phaeosphaeria nodorum* SN15] >gi|111055053|gb|EAT76173.1| hypothetical
protein SNOG_16475 [*Phaeosphaeria nodorum* SN15]
>gi|169783766|ref|XP_001826345.1| heat shock protein 60 [*Aspergillus oryzae*
RIB40] >gi|238493601|ref|XP_002378037.1| antigenic mitochondrial protein
HSP60, putative [*Aspergillus flavus* NRRL3357] >gi|83775089|dbj|BAE65212.1|
unnamed protein product [*Aspergillus oryzae* RIB40]
>gi|220696531|gb|EED52873.1| antigenic mitochondrial protein HSP60, putative
[*Aspergillus flavus* NRRL3357] >gi|391869413|gb|EIT78611.1| chaperonin,
Cpn60/Hsp60p [*Aspergillus oryzae* 3.042]
>gi|189190432|ref|XP_001931555.1| heat shock protein 60, mitochondrial
precursor [*Pyrenophora tritici-repentis* Pt-1C-BFP]
>gi|187973161|gb|EDU40660.1| heat shock protein 60, mitochondrial precursor
[*Pyrenophora tritici-repentis* Pt-1C-BFP]
>gi|190348913|gb|EDK41467.2| heat shock protein 60, mitochondrial precursor
[*Meyerozyma guilliermondii* ATCC 6260]
>gi|225554633|gb|EEH02929.1|hsp60-like protein [*Ajellomyces capsulatus*
G186AR]
>gi|238880068|gb|EEQ43706.1| heat shock protein 60, mitochondrial precursor
[*Candida albicans* WO-1]
>gi|239613490|gb|EEQ90477.1| chaperonin GroL [*Ajellomyces dermatitidis* ER-3]
>gi|240276977|gb|EER40487.1| hsp60-like protein [*Ajellomyces capsulatus* H143]
>gi|241958890|ref|XP_002422164.1| heat shock protein 60, mitochondrial
precursor, putative [*Candida dubliniensis* CD36] >gi|223645509|emb|CAX40168.1|
heat shock protein 60, mitochondrial precursor, putative [*Candida dubliniensis*
CD36]
>gi|254572906|ref|XP_002493562.1| Tetradecameric mitochondrial chaperonin
[*Komagataella pastoris* GS115] >gi|238033361|emb|CAY71383.1| Tetradecameric
mitochondrial chaperonin [*Komagataella pastoris* GS115]
>gi|254579947|ref|XP_002495959.1| ZYRO0C07106p [*Zygosaccharomyces rouxii*]
>gi|238938850|emb|CAR27026.1| ZYRO0C07106p [*Zygosaccharomyces rouxii*]
>gi|255712781|ref|XP_002552673.1| KLTH0C10428p [*Lachancea thermotolerans*]
>gi|238934052|emb|CAR22235.1| KLTH0C10428p [*Lachancea thermotolerans*
CBS 6340]
>gi|255721795|ref|XP_002545832.1| heat shock protein 60, mitochondrial
precursor [*Candida tropicalis* MYA-3404] >gi|240136321|gb|EER35874.1| heat
shock protein 60, mitochondrial precursor [*Candida tropicalis* MYA-3404]
>gi|255941288|ref|XP_002561413.1| Pc16g11070 [*Penicillium chrysogenum*
Wisconsin 54-1255] >gi|211586036|emb|CAP93777.1| Pc16g11070 [*Penicillium chrysogenum* Wisconsin 54-1255]
>gi|259148241|emb|CAY81488.1| Hsp60p [*Saccharomyces cerevisiae* EC1118]
>gi|260950325|ref|XP_002619459.1| heat shock protein 60, mitochondrial
precursor [*Clavispora lusitaniae* ATCC 42720] >gi|238847031|gb|EEQ36495.1|
heat shock protein 60, mitochondrial precursor [*Clavispora lusitaniae* ATCC 42720]
>gi|261194577|ref|XP_002623693.1| chaperonin GroL [*Ajellomyces dermatitidis*
SLH14081] >gi|239588231|gb|EEQ70874.1| chaperonin GroL [*Ajellomyces dermatitidis* SLH14081] >gi|327355067|gb|EGE83924.1| chaperonin GroL
[*Ajellomyces dermatitidis* ATCC 18188]
>gi|296422271|ref|XP_002840685.1| hypothetical protein [*Tuber melanosporum*
Mel28] >gi|295636906|emb|CAZ84876.1| unnamed protein product [*Tuber melanosporum*]
>gi|296809035|ref|XP_002844856.1| heat shock protein 60 [*Arthroderma otae* CBS
113480] >gi|238844339|gb|EEQ34001.1| heat shock protein 60 [*Arthroderma otae*
CBS 113480]
>gi|302308696|ref|NP_985702.2| AFR155Wp [*Ashbya gossypii* ATCC 10895]
>gi|299790751|gb|AAS53526.2| AFR155Wp [*Ashbya gossypii* ATCC 10895]
>gi|374108933|gb|AEY97839.1| FAFR155Wp [*Ashbya gossypii* FDAG1]
>gi|302412525|ref|XP_003004095.1| heat shock protein [*Verticillium albo-atrum*
VaMs.102] >gi|261356671|gb|EEY19099.1| heat shock protein [*Verticillium albo-atrum* VaMs.102]
>gi|302505585|ref|XP_003014499.1| hypothetical protein ARB_07061
[*Arthroderma benhamiae* CBS 112371] >gi|291178320|gb|EFE34110.1|
hypothetical protein ARB_07061 [*Arthroderma benhamiae* CBS 112371]
>gi|302656385|ref|XP_003019946.1| hypothetical protein TRV_05992
[*Trichophyton verrucosum* HKI 0517] >gi|291183723|gb|EFE39322.1| hypothetical
protein TRV_05992 [*Trichophyton verrucosum* HKI 0517]
>gi|302915513|ref|XP_003051567.1| predicted protein [*Nectria haematococca*
mpVI 77-13-4] >gi|256732506|gb|EEU45854.1| predicted protein [*Nectria haematococca* mpVI 77-13-4]
>gi|310794550|gb|EFQ30011.1| chaperonin GroL [*Glomerella graminicola* M1.001]

TABLE 4-continued

Natural chaperones homologous to GroEL polypeptides suitable for expression

>gi|315048491|ref|XP_003173620.1| chaperonin GroL [*Arthroderma gypseum* CBS 118893] >gi|311341587|gb|EFR00790.1| chaperonin GroL [*Arthroderma gypseum* CBS 118893]
>gi|320580028|gb|EFW94251.1| Tetradecameric mitochondrial chaperonin [*Ogataea parapolymorpha* DL-1]
>gi|320586014|gb|EFW98693.1| heat shock protein mitochondrial precursor [*Grosmannia clavigera* kw1407]
>gi|322692465|gb|EFY84374.1| heat shock protein 60 precursor (Antigen HIS-62) [*Metarhizium acridum* CQMa 102]
>gi|322705285|gb|EFY96872.1| heat shock protein 60 (Antigen HIS-62) [*Metarhizium anisopliae* ARSEF 23]
>gi|323303806|gb|EGA57589.1| Hsp60p [*Saccharomyces cerevisiae* FostersB]
>gi|323307999|gb|EGA61254.1| Hsp60p [*Saccharomyces cerevisiae* FostersO]
>gi|323332364|gb|EGA73773.1| Hsp60p [*Saccharomyces cerevisiae* AWRI796]
>gi|326468648|gb|EGD92657.1| heat shock protein 60 [*Trichophyton tonsurans* CBS 112818] >gi|326479866|gb|EGE03876.1| chaperonin GroL [*Trichophyton equinum* CBS 127.97]
>gi|330915493|ref|XP_003297052.1| hypothetical protein PTT_07333 [*Pyrenophora teres f. teres* 0-1] >gi|311330479|gb|EFQ94847.1| hypothetical protein PTT_07333 [*Pyrenophora teres f. teres* 0-1]
>gi|336271815|ref|XP_003350665.1| hypothetical protein SMAC_02337 [*Sordaria macrospora k-hell*] >gi|380094827|emb|CCC07329.1| unnamed protein product [*Sordaria macrospora k-hell*]
>gi|336468236|gb|EGO56399.1| hypothetical protein NEUTE1DRAFT_122948 [*Neurospora tetrasperma* FGSC 2508]
>gi|340522598|gb|EGR52831.1| hsp60 mitochondrial precursor-like protein [*Trichoderma reesei* QM6a]
>gi|341038907|gb|EGS23899.1| mitochondrial heat shock protein 60-like protein [*Chaetomium thermophilum* var. *thermophilum* DSM 1495]
>gi|342886297|gb|EGU86166.1| hypothetical protein FOXB_03302 [*Fusarium oxysporum* Fo5176]
>gi|344230084|gb|EGV61969.1| chaperonin GroL [*Candida tenuis* ATCC 10573]
>gi|344303739|gb|EGW33988.1| hypothetical protein SPAPADRAFT_59397 [*Spathaspora passalidarum* NRRL Y-27907]
>gi|345560428|gb|EGX43553.1| hypothetical protein AOL_s00215g289 [*Arthrobotrys oligospora* ATCC 24927]
>gi|346323592|gb|EGX93190.1| heat shock protein 60 (Antigen HIS-62) [*Cordyceps militaris* CM01]
>gi|346975286|gb|EGY18738.1| heat shock protein [*Verticillium dahliae* VdLs.17]
>gi|354545932|emb|CCE42661.1| hypothetical protein CPAR2_203040 [*Candida parapsilosis*]
>gi|358369894|dbj|GAA86507.1| heat shock protein 60, mitochondrial precursor [*Aspergillus kawachii* IFO 4308]
>gi|358386867|gb|EHK24462.1| hypothetical protein TRIVIDRAFT_79041 [*Trichoderma virens* Gv29-8]
>gi|358399658|gb|EHK48995.1| hypothetical protein TRIATDRAFT_297734 [*Trichoderma atroviride* IMI 206040]
>gi|363750488|ref|XP_003645461.1| hypothetical protein Ecym_3140 [*Eremothecium cymbalariae* DBVPG#7215]
>gi|356889095|gb|AET38644.1| Hypothetical protein Ecym_3140 [*Eremothecium cymbalariae* DBVPG#7215]
>gi|365759369|gb|EHN01160.1| Hsp60p [*Saccharomyces cerevisiae* × *Saccharomyces kudriavzevii* VIN7]
>gi|365764091|gb|EHN05616.1| Hsp60p [*Saccharomyces cerevisiae* × *Saccharomyces kudriavzevii* VIN7]
>gi|365985626|ref|XP_003669645.1| hypothetical protein NDAI_0D00880 [*Naumovozyma dairenensis* CBS 421]
>gi|343768414|emb|CCD24402.1| hypothetical protein NDAI_0D00880 [*Naumovozyma dairenensis* CBS 421]
>gi|366995970|ref|XP_003677748.1| hypothetical protein NCAS_0H00890 [*Naumovozyma castellii* CBS 4309]
>gi|342303618|emb|CCC71399.1| hypothetical protein NCAS_0H00890 [*Naumovozyma castellii* CBS 4309]
>gi|367005154|ref|XP_003687309.1| hypothetical protein TPHA_0J00520 [*Tetrapisispora phaffii* CBS 4417] >gi|357525613|emb|CCE64875.1| hypothetical protein TPHA_0J00520 [*Tetrapisispora phaffii* CBS 4417]
>gi|367017005|ref|XP_003683001.1| hypothetical protein TDEL_0G04230 [*Torulaspora delbrueckii*] >gi|359750664|emb|CCE93790.1| hypothetical protein TDEL_0G04230 [*Torulaspora delbrueckii*]
>gi|367035486|ref|XP_003667025.1| hypothetical protein MYCTH_2097570 [*Myceliophthora thermophila* ATCC 42464]
>gi|347014298|gb|AEO61780.1| hypothetical protein MYCTH_2097570 [*Myceliophthora thermophila* ATCC 42464]
>gi|367055018|ref|XP_003657887.1| hypothetical protein THITE_127923 [*Thielavia terrestris* NRRL 8126] >gi|347005153|gb|AEO71551.1| hypothetical protein THITE_127923 [*Thielavia terrestris* NRRL 8126]
>gi|378728414|gb|EHY54873.1| heat shock protein 60 [*Exophiala dermatitidis* NIH/UT8656]

TABLE 4-continued

Natural chaperones homologous to GroEL polypeptides suitable for expression

>gi|380494593|emb|CCF33032.1| heat shock protein 60 [*Colletotrichum higginsianum*]
>gi|385305893|gb|EIF49836.1| heat shock protein 60 [*Dekkera bruxellensis* AWRI1499]
>gi|389638386|ref|XP_003716826.1| heat shock protein 60 [*Magnaporthe oryzae* 70-15] >gi|351642645|gb|EHA50507.1| heat shock protein 60 [*Magnaporthe oryzae* 70-15] >gi|440474658|gb|ELQ43388.1| heat shock protein 60 [*Magnaporthe oryzae* Y34] >gi|440480475|gb|ELQ61135.1| heat shock protein 60 [*Magnaporthe oryzae* P131]
>gi|393243142|gb|EJD50658.1| chaperonin GroL [*Auricularia delicata* TFB-10046 SS5]
>gi|396494741|ref|XP_003844378.1| similar to heat shock protein 60 [*Leptosphaeria maculans* JN3] >gi|312220958|emb|CBY00899.1| similar to heat shock protein 60 [*Leptosphaeria maculans* JN3]
>gi|398393428|ref|XP_003850173.1| chaperone ATPase HSP60 [*Zymoseptoria tritici* IPO323] >gi|339470051|gb|EGP85149.1| hypothetical protein MYCGRDRAFT_75170 [*Zymoseptoria tritici* IPO323]
>gi|401624479|gb|EJS42535.1| hsp60p [*Saccharomyces arboricola* H-6]
>gi|401842294|gb|EJT44530.1| HSP60-like protein [*Saccharomyces kudriavzevii* IFO 1802]
>gi|402076594|gb|EJT72017.1| heat shock protein 60 [*Gaeumannomyces graminis* var. *tritici* R3-111a-1]
>gi|403213867|emb|CCK68369.1| hypothetical protein KNAG_0A07160 [*Kazachstania naganishii* CBS 8797]
>gi|406606041|emb|CCH42514.1| heat shock protein 60, mitochondrial [*Wickerhamomyces ciferrii*]
>gi|406863285|gb|EKD16333.1| heat shock protein 60 [*Marssonina brunnea* f. sp. 'multigermtubi' MB_m1]
>gi|407922985|gb|EKG16075.1| Chaperonin Cpn60 [*Macrophomina phaseolina* MS6]
>gi|408399723|gb|EKJ78816.1| hypothetical protein FPSE_00959 [*Fusarium pseudograminearum* CS3096]
>gi|410083028|ref|XP_003959092.1| hypothetical protein KAFR_0I01760 [*Kazachstania africana* CBS 2517] >gi|372465682|emb|CCF59957.1| hypothetical protein KAFR_0I01760 [*Kazachstania africana* CBS 2517]
>gi|444315528|ref|XP_004178421.1| hypothetical protein TBLA_0B00580 [*Tetrapisispora blattae* CBS 6284] >gi|387511461|emb|CCH58902.1| hypothetical protein TBLA_0B00580 [*Tetrapisispora blattae* CBS 6284]
>gi|448090588|ref|XP_004197110.1| Piso0_004347 [*Millerozyma farinosa* CBS 7064] >gi|448095015|ref|XP_004198141.1| Piso0_004347 [*Millerozyma farinosa* CBS 7064] >gi|359378532|emb|CCE84791.1| Piso0_004347 [*Millerozyma farinosa* CBS 7064] >gi|359379563|emb|CCE83760.1| Piso0_004347 [*Millerozyma farinosa* CBS 7064]
>gi|448526196|ref|XP_003869293.1| Hsp60 heat shock protein [*Candida orthopsilosis* Co 90-125] >gi|380353646|emb|CCG23157.1| Hsp60 heat shock protein [*Candida orthopsilosis*]
>gi|46123737|ref|XP_386422.1| HS60_AJECA Heat shock protein 60, mitochondrial precursor (Antigen HIS-62) [*Gibberella zeae* PH-1]
>gi|50292099|ref|XP_448482.1| hypothetical protein [*Candida glabrata* CBS 138] >gi|49527794|emb|CAG61443.1| unnamed protein product [*Candida glabrata*]
>gi|50310975|ref|XP_455510.1| hypothetical protein [*Kluyveromyces lactis* NRRL Y-1140] >gi|49644646|emb|CAG98218.1| KLLA0F09449p [*Kluyveromyces lactis*]
>gi|50422027|ref|XP_459575.1| DEHA2E05808p [*Debaryomyces hansenii* CBS767] >gi|49655243|emb|CAG87802.1| DEHA2E05808p [*Debaryomyces hansenii* CBS767]
>gi|50555023|ref|XP_504920.1| YALI0F02805p [*Yarrowia lipolytica*]
>gi|49650790|emb|CAG77725.1| YALI0F02805p [*Yarrowia lipolytica* CLIB122]
>gi|6323288|ref|NP_013360.1| Hsp60p [*Saccharomyces cerevisiae* S288c]
>gi|123579|sp|P19882.1| HSP60_YEAST RecName: Full = Heat shock protein 60, mitochondrial; AltName: Full = CPN60; AltName: Full = P66; AltName: Full = Stimulator factor I 66 kDa component; Flags: Precursor
>gi|171720|gb|AAA34690.1| heat shock protein 60 (HSP60) [*Saccharomyces cerevisiae*] >gi|577181|gb|AAB67380.1| Hsp60p: Heat shock protein 60 [*Saccharomyces cerevisiae*] >gi|151941093|gb|EDN59473.1| chaperonin [*Saccharomyces cerevisiae* YJM789] >gi|190405319|gb|EDV08586.1| chaperonin [*Saccharomyces cerevisiae* RM11-1a] >gi|207342889|gb|EDZ70518.1| YLR259Cp-like protein [*Saccharomyces cerevisiae* AWRI1631]
>gi|256271752|gb|EEU06789.1| Hsp60p [*Saccharomyces cerevisiae* JAY291]
>gi|285813676|tpg|DAA09572.1| TPA: chaperone ATPase HSP60 [*Saccharomyces cerevisiae* S288c] >gi|323353818|gb|EGA85673.1| Hsp60p [*Saccharomyces cerevisiae* VL3] >gi|349579966|dbj|GAA25127.1| K7_Hsp60p [*Saccharomyces cerevisiae* Kyokai no. 7] >gi|392297765|gb|EIW08864.1| Hsp60p [*Saccharomyces cerevisiae* CEN.PK113-7D] >gi|226279|prf||1504305A mitochondrial assembly factor
>gi|68485963|ref|XP_713100.1| heat shock protein 60 [*Candida albicans* SC5314]
>gi|68486010|ref|XP_713077.1| heat shock protein 60 [*Candida albicans* SC5314]

TABLE 4-continued

Natural chaperones homologous to GroEL polypeptides suitable for expression

>gi|6016258|sp|O74261.1| HSP60_CANAL RecName: Full = Heat shock protein 60, mitochondrial; AltName: Full = 60 kDa chaperonin; AltName: Full = Protein Cpn60; Flags: Precursor >gi|3552009|gb|AAC34885.1| heat shock protein 60 [*Candida albicans*] >gi|46434552|gb|EAK93958.1| heat shock protein 60 [*Candida albicans* SC5314] >gi|46434577|gb|EAK93982.1| heat shock protein 60 [*Candida albicans* SC5314]
>gi|71001164|ref|XP_755263.1| antigenic mitochondrial protein HSP60 [*Aspergillus fumigatus* Af293] >gi|66852901|gb|EAL93225.1| antigenic mitochondrial protein HSP60, putative [*Aspergillus fumigatus* Af293] >gi|159129345|gb|EDP54459.1| antigenic mitochondrial protein HSP60, putative [*Aspergillus fumigatus* A1163]
>gi|90970323|gb|ABE02805.1| heat shock protein 60 [*Rhizophagus intraradices*]

In an embodiment a 10 kDa chaperone from Table 3 is combined with a matching 60 kDa chaperone from Table 3 of the same organism genus or species for expression in the host. For instance: >gi|189189366|ref|XP_001931022.1|: 71-168 10 kDa chaperonin [*Pyrenophora tritici*-repentis] expressed together with matching >gi|189190432|ref|XP_001931555.1| heat shock protein 60, mitochondrial precursor [*Pyrenophora tritici*-repentis Pt-1C-BFP]. All other combinations from Table 3 and 4 similarly made with same organism source are also available to the skilled person for expression. Furthermore, one may combine a chaperone from Table 3 from one organism with a chaperone from Table 4 from another organism, or one may combine GroES with a chaperone from Table 3, or one may combine GroEL with a chaperone from Table 4.

The nucleic acid sequence encoding a molecular chaperone may encode a chaperone having an amino acid sequence according to SEQ ID NO: 3 and/or 4, or it or it is a functional homogue thereof having an amino acid sequence having at least 50%, at least 60%, at least 70% sequence identity with SEQ ID NO: 3 and/or 4; preferably at least 80%, at least 85%, 90%, at least 95%, at least 98%, at least 99% sequence identity with SEQ ID NO: 3 and/or 4, or it is a functional homologue which is derived, by way of one or more amino acid substitutions, deletions or insertions, from the amino acid sequence of SEQ ID NO: 3 and/or 4.

As follows from the above, the invention further relates to a method for preparing an organic compound comprising converting a carbon source, using a microorganism, thereby forming the organic compound. The method may be carried out under aerobic, oxygen-limited or anaerobic conditions.

The invention allows in particular a reduction in formation of an NADH dependent side-product, especially glycerol, by up to 100%, up to 99%, or up to 90%, compared to said production in a corresponding reference strain. The NADH dependent side-product formation is preferably reduced by more than 10% compared to the corresponding reference strain, in particular by at least 20%, more in particular by at least 50%. NADH dependent side-product production is preferably reduced by 10-100%, in particular by 20-95%, more in particular by 50-90%.

In an embodiment a fermentation process is provided, wherein Rubisco, or another enzyme capable of catalysing the formation of an organic compound from $CO_2$ (and another substrate) or another enzyme that catalyses the function of $CO_2$ as an electron acceptor, is used, and carbon dioxide is present in the gas mixture above the fermentation broth and/or dissolved in the fermentation broth. In a specific embodiment, the carbon dioxide or part thereof is formed in situ by the microorganism.

If desired, the method further comprises the step of adding external $CO_2$ to the reaction system, usually by aeration with $CO_2$ or a gas mixture containing $CO_2$, for instance a $CO_2$/nitrogen mixture. Adding external $CO_2$ in particular is used to (increase or) maintain the $CO_2$ within a desired concentration range, if no or insufficient $CO_2$ is formed in situ.

As a carbon source, in principle any carbon source that the microorganism can use as a substrate can be used. In particular an organic carbon source may be used, selected from the group of carbohydrates and lipids (including fatty acids). Suitable carbohydrates include monosaccharides, disaccharides, and hydrolysed polysaccharides (e.g. hydrolysed starches, lignocellulosic hydrolysates). Although a carboxylic acid may be present, it is not necessary to include a carboxylic acid such as acetic acid, as a carbon source.

The yeast of the invention is suitable for the production of an alcohol, notably ethanol. However, it is contemplated that the insight that $CO_2$ can be used as an electron acceptor in microorganisms that do not naturally allow this, has an industrial benefit for other biotechnological processes for the production of organic molecules, in particular organic molecules of a relatively low molecular weight, particularly organic molecules with a molecular weight below 1000 g/mol. The following items are mentioned herein as embodiments of the use of carbon dioxide as an electron acceptor in accordance with the invention.

Regarding the production of ethanol, details are found herein above, when describing the yeast cell comprising PRK and Rubisco and in the examples. The ethanol or another alcohol is preferably produced in a fermentative process.

For the production of several organic acids (carboxylates), e.g. citric acid, an aerobic process is useful. For citric acid production for instance *Aspergillus niger, Yarrowia lipolytica*, or another known citrate producing organism may be used.

An example of an organic acid that is preferably produced anaerobically is lactic acid. Various lactic acid producing bacterial strains and yeast strains that have been engineered for lactate production are generally known in the art. Other embodiments of the invention are now described in more detail.

In an embodiment the invention relates to the use of the recombinant yeast cell as described herein in fermentation in the biofuel industry. In an embodiment, the recombinant yeast cell may comprise one or two or more copies of one or more xylose isomerases and/or one or two or more copies of one or more xylose reductase and xylitol dehydrogenase genes, allowing the recombinant yeast cell to convert xylose. In an embodiment thereof, these genes may be integrated into the recombinant yeast cell genome. In another embodiment, the recombinant yeast cell comprises the genes araA, araB and araD. It is then able to ferment arabinose. In one embodiment of the invention the recombinant yeast cell comprises xylA-gene, XYL1 gene and XYL2 gene and/or XKS1-gene, to allow the recombinant yeast cell to ferment xylose; deletion of the aldose reductase (GRE3) gene and/or overexpression of GAL2 and/or deletion of GAL80. According to an embodiment, the following genes may be introduced in the recombinant yeast cell by introduction into a host cell:
1) a set consisting of PPP-genes TAL1, TKL1, RPE1 and RK/1, optionally under control of strong constitutive promoter;
2) a set consisting of a xylA-gene under under control of strong constitutive promoter;
3) a set comprising a XKS1-gene under control of strong constitutive promoter,
4) a set consisting of the genes araA, araB and araD under control of a strong constitutive promoter
5) deletion of an aldose reductase gene The above cells may be constructed using known recombinant expression techniques. The co-factor modification may be affected before, simultaneous or after any of the modifications 1) to 5). The recombinant yeast cell according to the invention may be subjected to evolutionary engineering to improve its properties. Evolutionary engineering processes are known processes. Evolutionary engineering is a process wherein industrially relevant phenotypes of a microorganism, herein the recombinant yeast cell, can be coupled to the specific growth rate and/or the affinity for a nutrient, by a process of rationally set-up natural selection. Evolutionary Engineering is for instance described in detail in Kuijper, M, et al, FEMS, Eukaryotic cell Research 5(2005) 925-934, WO2008/041840 and WO2009/112472. After the evolutionary engineering the resulting pentose fermenting recombinant yeast cell is isolated. The isolation may be executed in any known manner, e.g. by separation of cells from a recombinant yeast cell broth used in the evolutionary engineering, for instance by taking a cell sample or by filtration or centrifugation.

In an embodiment, the recombinant yeast cell is marker-free. As used herein, the term "marker" refers to a gene encoding a trait or a phenotype which permits the selection of, or the screening for, a host cell containing the marker. Marker-free means that markers are essentially absent in the recombinant yeast cell. Being marker-free is particularly advantageous when antibiotic markers have been used in construction of the recombinant yeast cell and are removed thereafter. Removal of markers may be done using any suitable prior art technique, e.g. intramolecular recombination.

In one embodiment, the industrial recombinant yeast cell is constructed on the basis of an inhibitor tolerant host cell, wherein the construction is conducted as described hereinafter. Inhibitor tolerant host cells may be selected by screening strains for growth on inhibitors containing materials, such as illustrated in Kadar et al, Appl. Biochem. Biotechnol. (2007), Vol. 136-140, 847-858, wherein an inhibitor tolerant S. cerevisiae strain ATCC 26602 was selected.

The recombinant yeast cell further may comprise those enzymatic activities required for conversion of pyruvate to a desired fermentation product, such as ethanol, butanol (e.g. n-butanol, 2-butanol and isobutanol), lactic acid, 3-hydroxypropionic acid, acrylic acid, acetic acid, succinic acid, citric acid, fumaric acid, malic acid, itaconic acid, an amino acid, 1,3-propane-diol, ethylene, glycerol, a ß-lactam antibiotic or a cephalosporin.

In an embodiment, the recombinant yeast cell is derived from an industrial recombinant yeast cell. An industrial cell and industrial recombinant yeast cell may be defined as follows. The living environments of (recombinant yeast cell) cells in industrial processes are significantly different from that in the laboratory. Industrial recombinant yeast cells must be able to perform well under multiple environmental conditions which may vary during the process. Such variations include change in nutrient sources, pH, ethanol concentration, temperature, oxygen concentration, etc., which together have potential impact on the cellular growth and ethanol production of Saccharomyces cerevisiae. Under adverse industrial conditions, the environmental tolerant strains should allow robust growth and production. Industrial recombinant yeast cell strains are generally more robust towards these changes in environmental conditions which may occur in the applications they are used, such as in the baking industry, brewing industry, wine making and the biofuel ethanol industry. In one embodiment, the industrial recombinant yeast cell is constructed on the basis of an industrial host cell, wherein the construction is conducted as described hereinafter. Examples of industrial yeast cell (S. cerevisiae) are Ethanol Red® (Fermentis) Fermiol® (DSM) and Thermosacc® (Lallemand).

The recombinant yeast cells according to the invention are preferably inhibitor tolerant, i.e. they can withstand common inhibitors at the level that they typically have with common pretreatment and hydrolysis conditions, so that the recombinant yeast cells can find broad application, i.e. it has high applicability for different feedstock, different pretreatment methods and different hydrolysis conditions. In an embodiment the recombinant yeast cell is inhibitor tolerant. Inhibitor tolerance is resistance to inhibiting compounds. The presence and level of inhibitory compounds in lignocellulose may vary widely with variation of feedstock, pretreatment method hydrolysis process. Examples of categories of inhibitors are carboxylic acids, furans and/or phenolic compounds. Examples of carboxylic acids are lactic acid, acetic acid or formic acid. Examples of furans are furfural and hydroxy-methylfurfural. Examples or phenolic compounds are vannilin, syringic acid, ferulic acid and coumaric acid. The typical amounts of inhibitors are for carboxylic acids: several grams per liter, up to 20 grams per liter or more, depending on the feedstock, the pretreatment and the hydrolysis conditions. For furans: several hundreds of milligrams per liter up to several grams per liter, depending on the feedstock, the pretreatment and the hydrolysis conditions. For phenolics: several tens of milligrams per liter, up to a gram per liter, depending on the feedstock, the pretreatment and the hydrolysis conditions.

In an embodiment, the recombinant yeast cell is a cell that is naturally capable of alcoholic fermentation, preferably, anaerobic alcoholic fermentation. A recombinant yeast cell preferably has a high tolerance to ethanol, a high tolerance to low pH (i.e. capable of growth at a pH lower than about 5, about 4, about 3, or about 2.5) and towards organic and/or a high tolerance to elevated temperatures.

The invention also relates to a process for the fermentation of a substrate to produce a fermentation product with a recombinant yeast cell as described herein, in the biofuel industry, wherein the glycerol yield is at least 5%, at least 10% or at least 10%, at least 20% or at least 30% lower than that of a process with the corresponding wild-type recombinant yeast cell. In an embodiment of such process, the ethanol yield is not increased or decreased, compared to that of a process with the corresponding wild-type recombinant yeast cell.

Any of the above characteristics or activities of a recombinant yeast cell may be naturally present in the cell or may be introduced or modified by genetic modification.

Recombinant Expression

The recombinant yeast cell is a recombinant cell. That is to say, a recombinant yeast cell comprises, or is transformed with or is genetically modified with a nucleotide sequence that does not naturally occur in the cell in question. Techniques for the recombinant expression of enzymes in a cell, as well as for the additional genetic modifications of a recombinant yeast cell are well known to those skilled in the art. Typically such techniques involve transformation of a cell with nucleic acid construct comprising the relevant sequence. Such methods are, for example, known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al., eds., "Current protocols in molecular biology", Green Publishing and Wiley Interscience, New York (1987). Methods for transformation and genetic modification of fungal host cells are known from e.g. EP-A-0635574, WO98/46772, WO 99/60102, WO00/37671, WO90/14423, EP-A-0481008, EP-A-0635574 and U.S. Pat. No. 6,265,186.

Bioproducts Production

Over the years suggestions have been made for the introduction of various organisms for the production of bio-ethanol from crop sugars. In practice, however, all major bio-ethanol production processes have continued to use the recombinant yeast cells of the genus *Saccharomyces* as ethanol producer. This is due to the many attractive features of *Saccharomyces* species for industrial processes, i. e. a high acid-, ethanol tolerance and osmotolerance, capability of anaerobic growth, and of course its high alcoholic fermentative capacity. In an embodiment, recombinant yeast cell species as host cells include *S. cerevisiae, S. bulderi, S. barnetti, S. exiguus, S. uvarum, S. diastaticus, K. lactis, K. marxianus* or *K. fragilis*. A recombinant yeast cell may be a cell suitable for the production of ethanol. A recombinant yeast cell may, however, be suitable for the production of fermentation products other than ethanol. Such non-ethanolic fermentation products include in principle any bulk or fine chemical that is producible by a eukaryotic microorganism such as a recombinant yeast cell or a filamentous fungus.

In an embodiment, recombinant yeast cell for production of non-ethanolic fermentation products is a host cell that contains a genetic modification that results in decreased alcohol dehydrogenase activity.

Lignocellulose

Lignocellulose, which may be considered as a potential renewable feedstock, generally comprises the polysaccharides cellulose (glucans) and hemicelluloses (xylans, heteroxylans and xyloglucans). In addition, some hemicellulose may be present as glucomannans, for example in wood-derived feedstocks. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucuronic acid and other hexoses and pentoses occurs under the action of different enzymes acting in concert. In addition, pectins and other pectic substances such as arabinans may make up considerably proportion of the dry mass of typically cell walls from non-woody plant tissues (about a quarter to half of dry mass may be pectins).

Pretreatment

Before enzymatic treatment, the lignocellulosic material may be pretreated. The pretreatment may comprise exposing the lignocellulosic material to an acid, a base, a solvent, heat, a peroxide, ozone, mechanical shredding, grinding, milling or rapid depressurization, or a combination of any two or more thereof. This chemical pretreatment is often combined with heat-pretreatment, e.g. between 150-220° C. for 1 to 30 minutes.

Enzymatic Hydrolysis

The pretreated material is commonly subjected to enzymatic hydrolysis to release sugars that may be fermented according to the invention. This may be executed with conventional methods, e.g. contacting with cellulases, for instance cellobiohydrolase(s), endoglucanase(s), beta-glucosidase(s) and optionally other enzymes. The conversion with the cellulases may be executed at ambient temperatures or at higher temperatures, at a reaction time to release sufficient amounts of sugar(s). The result of the enzymatic hydrolysis is hydrolysis product comprising C5/C6 sugars, herein designated as the sugar composition.

The Sugar Composition

The sugar composition used according to the invention comprises glucose and one or more pentose, e.g. arabinose and/or xylose. Any sugar composition may be used in the invention that suffices those criteria. Optional sugars in the sugar composition are galactose and mannose. In an embodiment, the sugar composition is a hydrolysate of one or more lignocellulosic material. Lignocelllulose herein includes hemicellulose and hemicellulose parts of biomass. Lignocellulose includes lignocellulosic fractions of biomass. Suitable lignocellulosic materials may be found in the following list: orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, switch grass, miscanthus, sweet sorghum, canola stems, soybean stems, prairie grass, gamagrass, foxtail; sugar beet pulp, citrus fruit pulp, seed hulls, cellulosic animal wastes, lawn clippings, cotton, seaweed, trees, softwood, hardwood, poplar, pine, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof. The conversion of glucose, xylose, arabinose and galactose to fermentation product is of great economic importance. Mannose is present in some lignocellulose materials be it usually in lower amounts than the previously mentioned sugars. Advantageously therefore also mannose is converted by the recombinant yeast cell. It is expected that recombinant yeast cells of the present invention can be further manipulated to achieve other desirable characteristics, or even higher overall ethanol yields. Selection of improved recombinant yeast cells by passaging the recombinant yeast cells on medium containing hydrolysate has resulted in improved recombinant yeast cell with enhanced fermentation rates. Using the teachings of the present invention, one could readily such improved strains. By pentose-containing material, it is meant any medium comprising pentose, whether liquid or solid. Suitable pentose-containing materials include hydrolysates of polysaccharide or lignocellulosic biomass such as corn hulls, wood, paper, agricultural byproducts, and the like.

By a "hydrolysate" as used herein, it is meant a polysaccharide that has been depolymerized through the addition of water to form mono and oligosaccharide sugars. Hydrolysates may be produced by enzymatic or acid hydrolysis of the polysaccharide-containing material.

Preferably, the recombinant yeast cell is able to grow under conditions similar to those found in industrial sources of pentose. The method of the present invention would be most economical when the pentose-containing material can be inoculated with the recombinant yeast cell variant without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors naturally present in the wood which inhibit or prevent the growth of most organisms. The examples below describe the fermentation of pentose in acid hydrolysates (or sulfite waste liquor) of hard woods and soft woods by the recombinant yeast cells of the present invention. It is reasonably expected that recombinant yeast cell strains capable of growing in sulfite waste liquor could grow be expected grow in virtually any other biomass hydrolysate.

Propagation

The invention further relates to a process for aerobic propagation of the recombinant yeast cell, in particular aerobic propagation of the recombinant yeast cell strain. Propagation is herein any process of recombinant yeast cell growth that leads to increase of an initial recombinant yeast cell population. Main purpose of propagation is to increase a recombinant yeast cell population using the recombinant yeast cell's natural reproduction capabilities as living organisms. There may be other reasons for propagation, for instance, in case dry recombinant yeast cell is used, propagation is used to rehydrate and condition the recombinant yeast cell, before it is grown. Fresh recombinant yeast cell, whether active dried recombinant yeast cell or wet cake may be added to start the propagation directly. The conditions of propagation are critical for optimal recombinant yeast cell production and subsequent fermentation, such as for example fermentation of lignocellulosic hydrolysate into ethanol. They include adequate carbon source, aeration, temperature and nutrient additions. Tank size for propagation and is normally between 2 percent and 5 percent of the (lignocellulosic hydrolysate to ethanol) fermentor size. In the propagation the recombinant yeast cell needs a source of carbon. The source of carbon may herein comprise glycerol, ethanol, acetate and/or sugars (C6 and C5 sugars). Other carbon sources may also be used. The carbon source is needed for cell wall biosynthesis and protein and energy production. Propagation is an aerobic process, therefore the propagation tank must be properly aerated to maintain a certain level of dissolved oxygen. Adequate aeration is commonly achieved by air inductors installed on the piping going into the propagation tank that pull air into the propagation mix as the tank fills and during recirculation. The capacity for the propagation mix to retain dissolved oxygen is a function of the amount of air added and the consistency of the mix, which is why water is often added at a ratio of between 50:50 to 90:10 mash to water. "Thick" propagation mixes (80:20 mash-to-water ratio and higher) often require the addition of compressed air to make up for the lowered capacity for retaining dissolved oxygen. The amount of dissolved oxygen in the propagation mix is also a function of bubble size, so some ethanol plants add air through spargers that produce smaller bubbles compared to air inductors. Along with lower glucose, adequate aeration is important to promote aerobic respiration, which differs from the comparably anaerobic environment of fermentation. One sign of inadequate aeration or high glucose concentrations is increased ethanol production in the propagation tank. Generally during propagation, recombinant yeast cell requires a comfortable temperature for growth and metabolism, for instance the temperature in the propagation reactor is between 25-40° C. Generally lower temperatures result in slower metabolism and reduced reproduction, while higher temperatures can cause production of stress compounds and reduced reproduction. In an embodiment the propagation tanks are indoors and protected from the insult of high summer or low winter temperatures, so that maintaining optimum temperatures of between within the range of 30-35 degrees C. is usually not a problem. Further propagation may be conducted as propagation of recombinant yeast cell is normally conducted.

Fermentation

The invention provides a process for the fermentation of a recombinant yeast cell according to the invention e.g. ethanol, that is advantageous in the biofuel industry.

In an embodiment, the recombinant yeast cell according to the invention may be a pentose and glucose fermenting recombinant yeast cell, including but not limited to such cells that are capable of anaerobic simultaneous pentose and glucose consumption. In an embodiment of the process the pentose-containing material comprises a hydrolysate of ligno-cellulosic material. The hydrolysate may be an enzymatic hydrolysate of ligno-cellulosic material.

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many micro-organisms use pyruvate or one of its derivatives as an electron and hydrogen acceptor thereby regenerating $NAD^+$.

Thus, in an embodiment, anaerobic fermentation process pyruvate is used as an electron (and hydrogen acceptor) and is reduced to fermentation products such as ethanol, butanol, lactic acid, 3-hydroxy-propionic acid, acrylic acid, acetic acid, succinic acid, malic acid, fumaric acid, an amino acid and ethylene.

The fermentation process is preferably run at a temperature that is optimal for the cell. Thus, for most recombinant yeast cells, the fermentation process is performed at a temperature which is less than about 50° C., less than about 42° C., or less than about 38° C. For recombinant yeast cell or filamentous fungal host cells, the fermentation process is preferably performed at a temperature which is lower than about 35, about 33, about 30 or about 28° C. and at a temperature which is higher than about 20, about 22, or about 25° C.

The ethanol yield on xylose and/or glucose in the process preferably is at least about 50, about 60, about 70, about 80, about 90, about 95 or about 98%. The ethanol yield is herein defined as a percentage of the theoretical maximum yield.

The invention also provides a process for producing a fermentation product. The fermentation process according to the present invention may be run under aerobic and anaerobic conditions. In an embodiment, the process is carried out under micro-aerophilic or oxygen limited conditions. An anaerobic fermentation process is herein defined as a fermentation process run in the absence of oxygen or in which substantially no oxygen is consumed, preferably less than about 5, about 2.5 or about 1 mmol/L/h, and wherein organic molecules serve as both electron donor and electron acceptors. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6, such as at least 7 mmol/L/h. A process of the invention may comprise recovery of the fermentation product. In an embodiment of the process, the cell ferments both the xylose and glucose, preferably simultaneously in which case preferably a cell is used which is insensitive to glucose repression to prevent diauxic growth. In addition to a source of xylose (and glucose) as carbon source, the fermentation medium will further comprise the appropriate ingredient required for growth of the cell. Compositions of fermentation media for growth of microorganisms such as recombinant yeast cells are well known in the art. The fermentation processes may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. These processes are described hereafter in more detail.

SSF Mode

For Simultaneous Saccharification and Fermentation (SSF) mode, the reaction time for liquefaction/hydrolysis or presaccharification step is dependent on the time to realize a desired yield, i.e. cellulose to glucose conversion yield. Such yield is preferably as high as possible, preferably 60% or more, 65% or more, 70% or more, 75% or more 80% or more, 85% or more, 90% or more, 95% or more, 96% or more, 97% or more, 98% or more, 99% or more, even 99.5% or more or 99.9% or more. According to the invention very high sugar concentrations in SHF mode and very high product concentrations (e.g. ethanol) in SSF mode are realized. In SHF operation the glucose concentration is 25 g/L or more, 30 g/L or more, 35 g/L or more, 40 g/L or more, 45 g/L or more, 50 g/L or more, 55 g/L or more, 60 g/L or more, 65 g/L or more, 70 g/L or more, 75 g/L or more, 80 g/L or more, 85 g/L or more, 90 g/L or more, 95 g/L or more, 100 g/L or more, 110 g/L or more, 120 g/L or more or may e.g. be 25 g/L-250 g/L, 30 gl/L-200 g/L, 40 g/L-200 g/L, 50 g/L-200 g/L, 60 g/L-200 g/L, 70 g/L-200 g/L, 80 g/L-200 g/L, 90 g/L-200 g/L.

Product Concentration in SSF Mode

In SSF operation, the product concentration (g/L) is dependent on the amount of glucose produced, but this is not visible since sugars are converted to product in the SSF, and product concentrations can be related to underlying glucose concentration by multiplication with the theoretical maximum yield (Yps max in gr product per gram glucose). The theoretical maximum yield (Yps max in gr product per gram glucose) of a fermentation product can be derived from textbook biochemistry. For ethanol, 1 mole of glucose (180 gr) yields according to normal glycolysis fermentation pathway in recombinant yeast cell 2 moles of ethanol (=2×46=92 gr ethanol. The theoretical maximum yield of ethanol on glucose is therefore 92/180=0.511 gr ethanol/gr glucose). For n-butanol (MW 74 gr/mole) or iso butanol, the theoretical maximum yield is 1 mole of butanol per mole of glucose. So Yps max for (iso-)butanol=74/180=0.411 gr (iso-)butanol/gr glucose. For lactic acid the fermentation yield for homolactic fermentation is 2 moles of lactic acid (MW=90 gr/mole) per mole of glucose. According to this stoichiometry, the Yps max=1 gr lactic acid/gr glucose. Similar calculation may be made for C5/C6 fermentations, in which in addition to glucose also pentoses are included e.g. xylose and/or arabinose. For other fermentation products a similar calculation may be made.

SSF Mode

In SSF operation the product concentration is 25 g*Yps g/L/L or more, 30*Yps g/L or more, 35 g*Yps/L or more, 40*Yps g/L or more, 45*Yps g/L or more, 50*Yps g/L or more, 55*Yps g/L or more, 60*Yps g/L or more, 65*Yps g/L or more, 70*Yps g/L or more, 75*Yps g/L or more, 80*Yps g/L or more, 85*Yps g/L or more, 90*Yps g/L or more, 95*Yps g/L or more, 100*Yps g/L or more, 110*Yps g/L or more, 120 g/L*Yps or more or may e.g. be 25*Yps g/L-250*Yps g/L, 30*Yps gl/L-200*Yps g/L, 40*Yps g/L-200*Yps g/L, 50*Yps g/L-200*Yps g/L, 60*Yps g/L-200*Yps g/L, 70*Yps g/L-200*Yps g/L, 80*Yps g/L-200*Yps g/L, 90*Yps g/L, 80*Yps g/L-200*Yps g/L. Accordingly, the invention provides a method for the preparation of a fermentation product, which method comprises:

a. degrading lignocellulose using a method as described herein; and b. fermenting the resulting material, thereby to prepare a fermentation product.

Fermentation Product

The fermentation product of the invention may be any useful product. In one embodiment, it is a product selected from the group consisting of ethanol, n-butanol, 2-butanol, isobutanol, lactic acid, 3-hydroxy-propionic acid, acrylic acid, acetic acid, succinic acid, fumaric acid, malic acid, itaconic acid, maleic acid, citric acid, adipic acid, an amino acid, such as lysine, methionine, tryptophan, threonine, and aspartic acid, 1,3-propane-diol, ethylene, glycerol, a β-lactam antibiotic and a cephalosporin, vitamins, pharmaceuticals, animal feed supplements, specialty chemicals, chemical feedstocks, plastics, solvents, fuels, including biofuels and biogas or organic polymers, and an industrial enzyme, such as a protease, a cellulase, an amylase, a glucanase, a lactase, a lipase, a lyase, an oxidoreductases, a transferase or a xylanase.

Recovery of the Fermentation Product

For the recovery of the fermentation product existing technologies are used. For different fermentation products different recovery processes are appropriate. Existing methods of recovering ethanol from aqueous mixtures commonly use fractionation and adsorption techniques. For example, a beer still can be used to process a fermented product, which contains ethanol in an aqueous mixture, to produce an enriched ethanol-containing mixture that is then subjected to fractionation (e.g., fractional distillation or other like techniques). Next, the fractions containing the highest concentrations of ethanol can be passed through an adsorber to remove most, if not all, of the remaining water from the ethanol. In an embodiment in addition to the recovery of fermentation product, the yeast may be recycled. The following non-limiting examples are intended to be purely illustrative.

EXAMPLES

Example 1. Overexpression of PPP Genes and Deletion of GPD2 Gene

GPD2 was deleted by transforming *Saccharomyces cerevisiae* strain IMX774 (which strain is disclosed in WO2017/

216136) using an approach as described in pending European Patent Application EP16194660.3 and pending PCT Application PCT/EP2017/076148 with DNA fragments resulting in a deletion of the GPD2 coding sequence upon homologous recombination in IMX774. This was accomplished by co-transforming the guide RNA expression plasmid with GPD2 targeting sequence, thereby abrogating the coding sequence of gpd2. The resulting strain was named IMX949.

Genes of the non-oxidative branch of the pentose-phosphate pathway (TAL1, NQM1, TKL1, TKL2, RPE1, RKI1) were overexpressed by transforming in *Saccharomyces cerevisiae* strain IMX774 (which strain is disclosed in WO2017/216136) using an approach as described in pending European Patent Application EP16194660.3 and pending PCT application PCT/EP2017/076148, with expression cassettes of the abovementioned genes under control of constitutive promoters.

The expression cassettes were integrated at the GPD2 locus by co-transforming the guide RNA expression plasmid with GPD2 targeting sequence, thereby abbrogating the coding sequence of gpd2. The resulting strain was named IMX1443. Strain IMX1443 was compared with IME324 and IMX774 in a batch fermentation experiment as described in WO2017/216136. Strain IME324 is disclosed in WO2017/216136.

Results are listed in Table 5 and 6.

TABLE 5

Results using yeast strain with PPP genes and deletion of GPD2 gene

| Relevant genotype | Strain | | | |
|---|---|---|---|---|
| | IME324 reference | IMX774 9*cbbM, DAN1p-prk, groES, groEL | IMX949 gpd2Δ 9*cbbm pDAN1-prk, groES, groEL | IMX1443 9*cbbM, DAN1p-prk, groES, groEL gpd2::RPE1, TKL1, TAL1, TAL2, RKI1, NQM1 |
| μ(h$^{-1}$) | 0.33 ± 0.01 | 0.20 ± 0.03 | 0.22 ± 0.01 | 0.30 ± 0.03 |
| Y glycerol/glucose (g g$^{-1}$) | 0.102 ± 0.001 | 0.058 ± 0.005 | 0.038 ± 0.001 | 0.014 ± 0.001 |
| Y biomass/glucose (g$_x$ g$^{-1}$) | 0.091 ± 0.000 | 0.087 ± 0.007 | 0.095 ± 0.004 | 0.096 ± 0.004 |
| Y EtOH/glucose (g g$^{-1}$) | 0.356 ± 0.004 | 0.409 ± 0.001 | 0.411 ± 0.002 | 0.420 ± 0.001 |
| Ratio glycerol produced/biomass (mmol g$_x^{-1}$) | 12.262 ± 0.122 | 7.272 ± 0.115 | 4.314 ± 0.245 | 1.557 ± 0.003 |

TABLE 6

Specific growth rates (μ), yields (Y) of biomass, ethanol and glycerol on glucose and stoichiometric relationships between glycerol production and biomass formation in anaerobic bioreactor batch cultures of *S. cerevisiae* strains IME369 and IMX1489. Cultures were grown on synthetic medium containing 20 g L$^{-1}$ glucose (pH 5). Specific growth rates and stoichiometries were calculated from sample points during the mid-exponential growth phase.

| | Strain | |
|---|---|---|
| Relevant Genotype | IME369 GPD1 GPD2 | IMX1489 GPD1 gpd2Δ pDAN1-prk cbbm non-ox PPP↑ |
| μ(h$^{-1}$) | 0.31 ± 0.00 | 0.30 ± 0.01 |
| Y biomass/glucose (g g$^{-1}$) | 0.091 ± 0.009 | 0.096 ± 0.01 * |
| Y ethanol/glucose (g g$^{-1}$) | 0.376 ± 0.005 | 0.421 ± 0.002 * |
| Y glycerol/glucose (g g$^{-1}$) | 0.107 ± 0.004 | 0.014 ± 0.000 ** |

TABLE 6-continued

Specific growth rates (μ), yields (Y) of biomass, ethanol and glycerol on glucose and stoichiometric relationships between glycerol production and biomass formation in anaerobic bioreactor batch cultures of *S. cerevisiae* strains IME369 and IMX1489. Cultures were grown on synthetic medium containing 20 g L$^{-1}$ glucose (pH 5). Specific growth rates and stoichiometries were calculated from sample points during the mid-exponential growth phase.

| | Strain | |
|---|---|---|
| Relevant Genotype | IME369 GPD1 GPD2 | IMX1489 GPD1 gpd2Δ pDAN1-prk cbbm non-ox PPP↑ |
| Glycerol produced/biomass (mmol (g biomass)$^{-1}$) | 12.189 ± 1.080 | 1.669 ± 0.082 ** |

Values represent averages ± mean deviations of measurements on independent duplicate cultures.
* (p < 0.02) and
** (p < 0.01) denote statistical significance of differences between IME324 (Table 5) and strains IME369 and IMX1489 in Student's t-tests. Degree of reduction balances constructed over the exponential growth phase yielded electron recoveries between 96% and 100%.

TABLE 7

Brief description of the sequence listing

| SEQ ID NO | Primer |
|---|---|
| 1 | *T. denitrificans* Rubisco large subunit CbbM |
| 2 | *S. oleracea* phosphoribulokinase (prk) |
| 3 | *E. coli* groES |
| 4 | *E. coli* groEL |

REFERENCE LIST

1. Entian K D, Kötter P. Yeast genetic strain and plasmid collections. Method Microbiol. 2007; 629-66.
2. Nijkamp J F, van den Broek M, Datema E, de Kok S, Bosman L, Luttik M A, Daran-Lapujade P, Vongsangnak W, Nielsen J, Heijne W H M, Klaassen P, Paddon C J, Platt D, Kötter P, van Ham R C, Reinders M J T, Pronk J T, de Ridder D, Daran J-M. De novo sequencing, assembly and analysis of the genome of the laboratory strain *Saccharomyces cerevisiae* CEN.PK113-7D, a model for modern industrial biotechnology. Microb Cell Fact. 2012; 11:36.
3. Verduyn C, Postma E, Scheffers W A, van Dijken J P. Effect of benzoic acid on metabolic fluxes in yeasts: A continuous-culture study on the regulation of respiration and alcoholic fermentation. Yeast. 1992; 8:501-17.
4. Mans R, van Rossum H M, Wijsman M, Backx A, Kuijpers N G, van den Broek M, Daran-Lapujade P, Pronk J T, van *Maris* AJA, Daran J-M. CRISPR/Cas9: a molecular Swiss army knife for simultaneous introduction of multiple genetic modifications in *Saccharomyces cerevisiae*. FEMS Yeast Res. 2015; 15:fov004.
5. DiCarlo J E, Norville J E, *Mali* P, Rios X, Aach J, Church G M. Genome engineering in *Saccharomyces cerevisiae* using CRISPR-Cas systems. Nucleic Acids Res. 2013; 1-8.
6. Mikkelsen M D, Buron L D, Salomonsen B, Olsen C E, Hansen B G, Mortensen U H, Halkier B A. Microbial production of indolylglucosinolate through engineering of a multi-gene pathway in a versatile yeast expression platform. Metab Eng. 2012; 14:104-11.
7. Knijnenburg T A, Daran J M, van den Broek M A, Daran-Lapujade P A, de Winde J H, Pronk J T, Reinders M J, Wessels L F. Combinatorial effects of environmental parameters on transcriptional regulation in *Saccharomyces cerevisiae*: A quantitative analysis of a compendium of chemostat-based transcriptome data. BMC Genomics. 2009; 10:53.
8. Mumberg D, Müller R, Funk M. Yeast vectors for the controlled expression of heterologous proteins in different genetic backgrounds. Gene. 1995; 156:119-22.
9. Gueldener U, Heinisch J, Koehler G J, Voss D, Hegemann J H. A second set of loxP marker cassettes for Cre-mediated multiple gene knockouts in budding yeast. Nucleic Acids Res. 2002; 30:e23.
10. Guadalupe-Medina V, Wisselink H, Luttik M, de Hulster E, Daran J-M, Pronk J T, van *Maris* AJA. Carbon dioxide fixation by Calvin-Cycle enzymes improves ethanol yield in yeast. Biotechnol Biofuels. 2013; 6:125.
11. Daniel Gietz R, Woods R A: Transformation of yeast by lithium acetate/single-stranded carrier DNA/polyethylene glycol method. Methods Enzymol. 2002:87-96.
12. Solis-Escalante D, Kuijpers N G A, Bongaerts N, Bolat I, Bosman L, Pronk J T, Daran J-M, Daran-Lapujade P. amdSYM, a new dominant recyclable marker cassette for *Saccharomyces cerevisiae*. FEMS Yeast Res. 2013; 13:126-39.
13. Guadalupe-Medina V, Almering M J H, van *Maris* AJA, Pronk J T. Elimination of glycerol production in anaerobic cultures of a *Saccharomyces cerevisiae* strain engineered to use acetic acid as an electron acceptor. Appl Environ Microb. 2010; 76:190-5.
14. Papapetridis I, van Dijk M, Dobbe A P, Metz B, Pronk J T, van *Maris* AJA. Improving ethanol yield in acetate-reducing *Saccharomyces cerevisiae* by cofactor engineering of 6-phosphogluconate dehydrogenase and deletion of ALD6. Microb Cell Fact. 2016; 15:1-16.
15. Heijnen J J, van Dijken J P. In search of a thermodynamic description of biomass yields for the chemotrophic growth of microorganisms. Biotechnol Bioeng. 1992; 39:833-58.
16. Postma E, Verduyn C, Scheffers W A, van Dijken J P. Enzymic analysis of the crabtree effect in glucose-limited chemostat cultures of *Saccharomyces cerevisiae*. Appl Environ Microbiol. 1989; 55:468-77.
17. Verduyn C, Postma E, Scheffers W A, van Dijken J P. Physiology of *Saccharomyces cerevisiae* in anaerobic glucose-limited chemostat cultures. J Gen Microbiol. 1990; 136:395-403.
18. Kwast et al. Genomic Analysis of Anaerobically induced genes in *Saccharomyces cerevisiae*: Functional roles of ROX1 and other factors in mediating the anoxic response, 2002, Journal of bacteriology vol 184, no1 p 250-265.
19. Keng, T. 1992. HAP1 and ROX1 form a regulatory pathway in the repression of HEM13 transcription in *Saccharomyces cerevisiae*. Mol. Cell. Biol. 12: 2616-2623.
20. Labbe-Bois, R., and P. Labbe. 1990. Tetrapyrrole and heme biosynthesis in the yeast *Saccharomyces cerevisiae*, p. 235-285. In H. A. Dailey (ed.), Biosynthesis of heme and chlorophylls. McGraw-Hill, New York, N.Y.
21. Zitomer, R. S., and C. V. Lowry. 1992. Regulation of gene expression by oxygen in *Saccharomyces cerevisiae*. Microbiol. Rev. 56:1-11.
22. Zitomer, R. S., P. Carrico, and J. Deckert. 1997. Regulation of hypoxic gene expression in yeast. Kidney Int. 51:507-513.
23. Cohen et al., Induction and repression of DAN1 and the family of anaerobic mannoprotein genes in *Saccharomyces cerevisiae* occurs through a complex array of regulatory sites. Nucleic Acid Research, 2001 Vol. 29, No3, 799-808
24. Ter Kinde and de Steensma, A microarray-assisted screen for potential Hap1 and Rox1 target genes in *Saccharomyces cerevisiae*, 2002, Yeast 19: 825-840.
25. Sertil et al. The DAN1 gene of *S cerevisiae* is regulated in parallel with the hypoxic gene, but by a different mechanism, 1997, Gene Vol 192, pag 199-205.

The invention claimed is:

1. A recombinant yeast cell functionally expressing one or more heterologous nucleic acid sequences encoding for ribulose-1,5-phosphate carboxylase/oxygenase (Rubisco) having EC number 4.1.1.39 and further comprising one or more phosphoribulokinase (PRK) having EC number 2.7.1.19, wherein:

one or more genes of the non-oxidative branch of the pentose phosphate pathway, and encoding an enzyme selected from the group consisting of transaldolase having EC number 2.2.1.2, transketolase having EC number 2.2.1.1, ribose-5-phosphate isomerase having EC number 5.3.1.6 and D-ribulose-5-phosphate 3-epimerase having EC number 5.1.3.1, are overexpressed;

the PRK is under control of a promoter which has a PRK expression ratio$_{anaerobic/aerobic}$ of 2 or more; and the Rubisco and the one or more genes of the non-oxidative branch of the pentose phosphate pathway are under control of one or more constitutive promoters, and the recombinant yeast cell further comprising a deletion or disruption of a glycerol-3-phosphate dehydrogenase (GPD) gene.

2. The recombinant yeast cell according to claim 1 wherein the GPD gene encodes for an enzyme having EC number 1.1.1.8.

3. The recombinant yeast cell according to claim 1 wherein the GPD gene comprises GPD1 and GPD2, and wherein the GPD1 and GPD2 are deleted or disrupted.

4. The recombinant yeast cell according to claim 1, wherein the one or more genes of the pentose phosphate pathway is selected from the group consisting of TAL1, TAL2, NQM1, TKL1, TKL2, RPE1, RKI1, or a combination thereof.

5. The recombinant yeast cell according to claim 1 wherein the yeast cell is selected from the group of Saccharomycetaceae.

6. A process for preparing an organic compound comprising culturing the recombinant yeast cell according to claim 1 with a carbon source, thereby forming the organic compound.

7. The process according to claim 6 wherein the carbon source is a starch hydrolysate.

8. The process according to claim 6 wherein the carbon source is a corn fiber hydrolysate.

9. The process according to claim 6 wherein the carbon source is a corn stover hydrolysate.

10. The recombinant yeast cell according to claim 1, wherein the one or more genes of the pentose phosphate pathway comprise RPE1, TKL1, TAL1, TAL2, RKI1, and NQM1.

11. The recombinant yeast cell according to claim 10, functionally expressing one or more heterologous nucleic acid sequences encoding one or more molecular chaperones for Rubisco.

12. The recombinant yeast cell according to claim 11, wherein the molecular chaperones for Rubisco are groES and groEL.

13. The recombinant yeast cell according to claim 1, wherein the promoter which has a PRK expression ratio$_{anaerobic/aerobic}$ of 2 or more is selected from the group consisting of FET4 (FErrous Transport: YMR319C), YHK8 (YHR048W), AAC3 (ADP/ATP Carrier: YBR085W), DIP5 (DIcarboxylic amino acid Permease; YPL265W), HEM13 (HEMe biosynthesis; YDR044W), YNR014W, YAR028W, FUN57, OYE2 (Old Yellow Enzyme; YHR179W), SUR2 (SUppressor of Rvs161 and rvs167 mutations; YDR297W), FRDS1 (Fumarate ReDuctase; YEL047C), PIS1 (Phosphatidyl Inositol Synthase; YPR113W), LAC1 (Longevity-Assurance gene Cognate (LAG1 Cognate); YKL008C), YGR035C, YAL028W, EUG1 (ER protein Unnecessary for Growth; YDR518W), HEM14 (HEMe biosynthesis; YER014W), ISU2 (IscU homolog; YOR226C), ERG26 (ERGosterol biosynthesis; YGL001C), YMR252C, SML1 (Suppressor of Mec Lethality; YML058W), PAU7 (YAR020C), PAU5 (YFL020C), YLL064C, YGR294W, YIL176C, YGL261C, YOL161C, PAU1 (YJL223C), PAU6 (YNR076W), YDR542W, YIR041W, YKL224C, PAU3 (YCR104W), YLL025W, YOR394W, YHL046C, YMR325W, YAL068C, YPL282C, PAU2 (YEL049W), and PAU4 (YLR461W).

14. The recombinant yeast cell according to claim 1, functionally expressing one or more heterologous nucleic acid sequences encoding one or more molecular chaperones for Rubisco, wherein the molecular chaperones for Rubisco are groES and groEL, wherein the promoter which has a PRK expression ratio$_{anaerobic/aerobic}$ of 2 or more is DAN1 (Delayed ANaerobic; YJR150C), and wherein the one or more genes of the pentose phosphate pathway comprise RPE1, TKL1, TAL1, TAL2, RKI1, and NQM1.

15. The process according to claim 6 wherein the organic compound is an alcohol.

16. The process according to claim 6 wherein the carbon source is a carbohydrate.

* * * * *